US010655179B2

(12) United States Patent
Hantash

(10) Patent No.: US 10,655,179 B2
(45) Date of Patent: May 19, 2020

(54) CYSTIC FIBROSIS TRANSMEMBRANE CONDUCTANCE REGULATOR GENE MUTATIONS

(71) Applicant: Quest Diagnostics Investments Incorporated, Wilmington, DE (US)

(72) Inventor: Feras Hantash, Mission Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 15/864,469

(22) Filed: Jan. 8, 2018

(65) Prior Publication Data

US 2018/0208987 A1 Jul. 26, 2018

Related U.S. Application Data

(60) Continuation of application No. 15/222,218, filed on Jul. 28, 2016, now Pat. No. 9,863,000, which is a continuation of application No. 12/909,141, filed on Oct. 21, 2010, now Pat. No. 9,422,606, which is a division of application No. 11/506,453, filed on Aug. 18, 2006, now Pat. No. 7,838,646.

(60) Provisional application No. 60/709,329, filed on Aug. 18, 2005.

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS 4,683,194 A 7/1987 Saiki et al.
4,683,202 A 7/1987 Mullis
4,956,778 A 9/1990 Naito
4,998,617 A 3/1991 Ladd et al.
5,130,238 A 7/1992 Malek et al.
5,169,766 A 12/1992 Schuster et al.
5,407,796 A 4/1995 Cutting et al.
5,567,586 A 10/1996 Croce
5,834,181 A 11/1998 Shuber
5,846,710 A 12/1998 Bajaj
5,885,775 A 3/1999 Haff et al.
5,888,819 A 3/1999 Goelet et al.
5,955,377 A 9/1999 Maul et al.
5,981,178 A 11/1999 Tsui et al.
5,981,714 A 11/1999 Cheng et al.
6,011,588 A 1/2000 Kim
6,288,220 B1 9/2001 Kambara et al.
6,355,429 B1 3/2002 Nygren et al.
6,403,320 B1 6/2002 Read et al.
6,406,844 B1 6/2002 Pirrung et al.
6,576,421 B1 * 6/2003 Westbrook .......... C12Q 1/6841 435/6.11
6,812,339 B1 11/2004 Venter et al.
8,338,578 B1 * 12/2012 McGinniss .......... C12Q 1/6883 536/23.1
2003/0235834 A1 * 12/2003 Dunlop ............... C12Q 1/6883 435/6.12
2004/0110138 A1 6/2004 Lem et al.
2004/0126760 A1 7/2004 Broude
2005/0059035 A1 * 3/2005 Huang .................. C07H 21/04 435/6.15
2008/0171332 A1 7/2008 Sun et al.

FOREIGN PATENT DOCUMENTS

EP 0 329 822 B1 6/1994
EP 0 237 362 B1 10/1998
EP 0 201 184 8/2004
WO WO-88/10315 12/1988
WO WO-89/06700 7/1989
WO WO-2004/040013 A1 5/2004

OTHER PUBLICATIONS

Cystic Fibrosis Mutation Database (Record for c.(?_744)_(1584_?)dup submitted Aug. 31, 2005 and found online at http://www.genet.sickkids.on.ca/MutationDetailPage.external?sp=1480 and viewed Apr. 25, 2019).*
Accession No. AF205406, published on Apr. 16, 2004.
Accession No. AY183426, published on Jan. 27, 2003.
Audrézet, et al., "Genomic Rearrangements in the CFTR Gene: Extensive Allelic Heterogeneity and Diverse Mutational Mechanisms" Hum Mutat. 23(4):343-357 (2004).
Boat, et al., "The Metabolic Basis of Inherited Disease" Membrane Transport Systems, 6th ed, 2649-2680 (1989).
Carvalho-Oliveira, et al., "CFTR Localization in Native Airway Cells and Cell Lines Expressing Wild-type of F508del-CFTR by a Panel of Different Antibodies", Journal of Histochemistry & Cytochemistry, 52(2): 193-203, (2004).
Castellani et al., "Consensus on the use and interpretation of cystic fibrosis mutation analysis in clinical practice", 2008, Journal of Cystic Fibrosis, vol. 7, pp. 179-196.
CF Genetic Analysis consortium newsletter #67 Jan. 5, 1996 http://www.genet.sickkids.on.ca/resource/nl.CFnewslet.67.html.
Chevalier-Porst et al., Identification of three rare frameshift mutations in exon 13 of the cystic fibrosis gene: 1918delGC, 2118del4 and 2372del8, Human Molecular Genetics, 2(7): 1071-1072, 1993.

(Continued)

*Primary Examiner* — Amanda Haney
(74) *Attorney, Agent, or Firm* — Foley & Lardner LLP

(57) ABSTRACT

The present invention provides novel mutations of the CFTR gene related to cystic fibrosis or to conditions associated with cystic fibrosis. The mutations include duplication of exons including duplication of exons 6b through 10. Methods of identifying if an individual contains the exons 6b through 10 duplication are provided as well as nucleic acid fragments that contain the junction site of the duplicated segment. The detection of additional mutations in the CFTR gene are also provided.

18 Claims, 3 Drawing Sheets

Specification includes a Sequence Listing.

(56) References Cited

OTHER PUBLICATIONS

Claass, et al., "Applicability of Different Antibodies for Immunohistochemical Localization of CFTR in Sweat Glands from Healthy Controls and from Patients with Cystic Fibrosis", The Journal of Histochemistry & Cytochemistry, 48(6): 831-837, (2000).
Cohn, et al., "CFTR: Development of High-Affinity Antibodies and Localization in Sweat Gland", Biochemical and Biophysical Research Communications, 181(1): 36-43, (1991).
Doucet, et al., "Applicability of Different Antibodies for the Immunohistochemical Localization of CFTR in Respiratory and Intestinal Tissues of Human and Murine Origin", 51(9): 1191-1199, (2003).
Ezquieta et al., "CF2603/4delT, a new frameshift mutation in exon 13 of the cystic fibrosis transmembrane conductance regulator (CFTR) gene", Human Genetics, 91:614-615, 1993.
Flanigan, et al., "Rapid Direct Sequence Analysis of the Dystrophin Gene", Am. J. Genet., 72:931-939, (2003).
Hantash, F. et al., "Consultations in Molecular Diagnostics. Characterization of a Recurrent Novel Large Duplication in the Cystic Fibrosis Transmembrane Conductance Regulator Gene", The Journal of Molecular Diagnostics, vol. 9, No. 4, Sep. 2007, p. 556-560.
Hoogendoorn, et al., "Genotyping Single Nucleotide Polymorphisms by Primer Extension and High Performance Liquid Chromatography", Human Genetics, 104:89-93 (1999).
Interview Summary dated Sep. 2, 2009 for U.S. Appl. No. 11/615,645.
Jenison, et al., "Use of a Thin Film Biosensor for Rapid Visual Detection of PCR Products in a Multiplex Format", Biosens Bioelectron, 16(9-12):757-763 (2001).
Kwoh, et al., "Transcription-based amplification system and detection of amplified human immunodeficiency virus type 1 with a bead-based sandwich hybridization format", Proc. Natl. Acad. Sci., 86:1173-1177 (1989).
Landegren et al., "A Ligase-Mediated Gene Detection Technique", Science, 241:1077-1080, (1988).
Mendes, et al., "Antibodies in CFTR Studies", Journal of Cystic Fibrosis, 3: 69-72, (2004).
Newton, et al., "Analysis of any Point Mutation in DNA. The Amplification Refractory Mutation System (ARMS)", Nucleic Acids Res., 17:2503-2516 (1989).
Nickerson, et al., "Automated DNA Diagnostics Using an ELISA-Based Oligonucleotide Litigate Assay", Proc. Natl. Acad. Sci. USA, 87:8923-8927 (1990).
Niel et al., "Rapid detection of CFTR gene rearrangements impacts on genetic counselling in cystic fibrosis," J. Med. Genet., vol. 41, p. e118, 2004.
Okayama, et al., "Rapid, nonradioactive detection of mutations in the human genome by allele-specific amplification", J. Lab. Clin. Med., 114:105-113, (1989).
Piggee, et al., "Capillary Electrophoresis for the Detection of Known Point Mutations by Single-Nucleotide Primer Extension and Laster-Induced Fluorescence Detection", Journal of Chromatography A 781:367-375 (1997).
Poddar, S.K., "Symmetric vs Asymmetric PCR and Molecular Beacon Probe in the Detection of a Target Gene of Adenovirus," Molec. and Cell. Probes, (2000), 14:25-32.
Ratjen and Doring, "Cystic Fibrosis", The Lancet, 361:681-689, 2003.
Romey et al., "Two novel rare frameshift mutations (2423 del G in exon 13 and 1215 del G in exon 7) and one novel rare sequence variation (3271 + 18 C or T) identified in a patient with cystic fibrosis", Human Molecular Genetics, 3(6): 1003-1004, 1994.
Rowntree et al., "The phenotypic consequences of CFTR mutations", 2003, Annals of Human Genetics, vol. 67, pp. 471-485.
Sarkar, et al., "Characterization of Polymerase Chain Reaction Amplification of Specific Alleles", Anal. Biochem. 186:64-68 (1990).
Sellner, et al., "MLPA and MAPH: New Techniques for Detection of Gene Deletions", Human Mutation 23:413-419 (2004).
Strom et al., "Extensive sequencing of the cystic fibrosis transmembrane regulator gene: Assay validation and unexpected benefits of developing a comprehensive test", Genetics in Medicine, 5(1):9-14 (2003).
Syvånen, "Accessing Genetic Variation: Genotyping Single Nucleotide Polymorphisms," Nature Reviews Genetics, vol. 2, pp. 930-942, Dec. 2001.
U.S. Final Office Action for U.S. Appl. No. 11/506,453 dated Jun. 6, 2008.
U.S. Notice of Allowance dated Nov. 13, 2009 for U.S. Appl. No. 11/615,645.
U.S. Office Action dated Mar. 9, 2009 for U.S. Appl. No. 11/938,138.
U.S. Office Action dated Jun. 13, 2008 for U.S. Appl. No. 11/615,645.
U.S. Office Action dated Jun. 26, 2009 for U.S. Appl. No. 11/615,645.
U.S. Office Action dated Aug. 8, 2007 for U.S. Appl. No. 11/506,453.
U.S. Office Action dated Oct. 31, 2007 for U.S. Appl. No. 11/506,453.
U.S. Office Action dated Nov. 24, 2008 for U.S. Appl. No. 11/615,645.
U.S. Office Action dated Dec. 11, 2008 for U.S. Appl. No. 11/506,453.
U.S. Office Action dated Jul. 7, 2009 for U.S. Appl. No. 11/938,138.
U.S. Advisory Action dated May 10, 2010 in related U.S. Appl. No. 11/938,138.
U.S. Notice of Allowance dated Oct. 24, 2017 in related U.S. Appl. No. 15/212,581.
U.S. Notice of Allowance dated Nov. 10, 2011 in related U.S. Appl. No. 12/847,960.
U.S. Notice of Allowance dated Feb. 10, 2014 in related U.S. Appl. No. 13/358,322.
U.S. Notice of Allowance dated Feb. 26, 2016 in related U.S. Appl. No. 14/304,087.
U.S. Notice of Allowance dated Apr. 19, 2016 in related U.S. Appl. No. 12/909,141.
U.S. Notice of Allowance dated Apr. 26, 2010 in related U.S. Appl. No. 11/615,645.
U.S. Notice of Allowance dated Jul. 9, 2010 in related U.S. Appl. No. 11/938,138.
U.S. Notice of Allowance dated Sep. 1, 2017 in related U.S. Appl. No. 15/222,218.
U.S. Notice of Allowance dated Sep. 2, 2010 in related U.S. Appl. No. 11/506,453.
U.S. Office Action dated Sep. 16, 2009 in related U.S. Appl. No. 11/506,453.
U.S. Office Action dated Jan. 9, 2015 in related U.S. Appl. No. 14/304,087.
U.S. Office Action dated Oct. 23, 2013 in related U.S. Appl. No. 13/358,322.
U.S. Office Action dated Nov. 30, 2012 in related U.S. Appl. No. 13/358,322.
U.S. Office Action dated Feb. 11, 2015 in related U.S. Appl. No. 12/909,141.
U.S. Office Action dated Feb. 21, 2014 in related U.S. Appl. No. 12/909,141.
U.S. Office Action dated Mar. 12, 2013 in related U.S. Appl. No. 13/358,322.
U.S. Office Action dated Mar. 23, 2015 in related U.S. Appl. No. 14/304,087.
U.S. Office Action dated Mar. 23, 2016 in related U.S. Appl. No. 12/909,141.
U.S. Office Action dated Apr. 2, 2010 in related U.S. Appl. No. 11/938,138.
U.S. Office Action dated Apr. 4, 2012 in related U.S. Appl. No. 13/358,322.
U.S. Office Action dated May 11, 2012 in related U.S. Appl. No. 13/358,322.
U.S. Office Action dated May 24, 2017 in related U.S. Appl. No. 15/212,581.
U.S. Office Action dated May 31, 2017 in related U.S. Appl. No. 15/222,218.
U.S. Office Action dated Jun. 15, 2011 in related U.S. Appl. No. 12/847,960.
U.S. Office Action dated Jun. 19, 2013 in related U.S. Appl. No. 13/358,322.
U.S. Office Action dated Jun. 24, 2014 in related U.S. Appl. No. 12/909,141.

(56) References Cited

OTHER PUBLICATIONS

U.S. Office Action dated Jul. 23, 2015 in related U.S. Appl. No. 14/304,087.
U.S. Office Action dated Aug. 18, 2015 in related U.S. Appl. No. 12/909,141.
Vankeerberghen et al., "The cystic fibrosis transmembrane conductance regulator: an intriguing protein with pleiotropic functions", Journal of Cystic Fibrosis, 1:13-20, 2002.
Walker, et al., "Isothermal in Vitro Amplification of DNA by a Restriction Enzyme/DNA Polymerase System", Proc. Natl. Acad. Sci. USA 89:392-396 (1992).
Walker, et al., "Production and characterisation of monoclonal and polyclonal antibodies to different regions of the cystic fibrosis transmembrane conductance regulator (CFTR): detection of immunologically related proteins", Journal of Cell Science, (1995), 108:2433-2444.
Wall, et al., "A 31-Mutation Assay for Cystic Fibrosis Testing in the Clinical Molecular Diagnostics Laboratory", Human Mutation 5(4):333-338 (1995).
Weiss et al., "Complete cystic fibrosis transmembrane conductance regular gene sequencing in patients with idiopathetic chronic pancreatitis and controls", 2005, Gut vol. 54:1456-1460.
Welsh et al., "Molecular mechanisms of CFTR chloride channel dysfunction in cystic fibrosis", Cell, 73: 1251-1254, 1993.
Wu, et al., "Allele-specific enzymatic amplification of 0-globin genomic DNA for diagnosis of sickle cell anemia", Proc. Natl. Acad. Sci. USA. 86:2757-2760 (1989).
Zielenski, et al., "Genomic DNA Sequence of the Cystic Fibrosis Transmembrane Conductane Regulator (CFTR) Gene", Genomics 10:214-228 (1991).
Notice of Allowance dated Aug. 7, 2019 in U.S. Appl. No. 15/910,681.
Office Action dated Jan. 23, 2019 in U.S. Appl. No. 15/910,681.

* cited by examiner

FIG. 1

| Exon | Location on Corresponding Genbank | Length in bp | IVS | Location on Corresponding Genbank | Length in bp | |
|---|---|---|---|---|---|---|
| 1 | 19760-19854 | 95 | 1 | 19855-43958 | 24104 | GenBank #AC000111 |
| 2 | 43959-44070 | 112 | 2 | 44071-48740 | 4670 | |
| 3 | 48741-48849 | 109 | 3 | 48850-70607 | 21758 | |
| 4 | 70606-70821 | 216 | 4 | 70822-73982 | 3161 | |
| 5 | 73983-74072 | 90 | 5 | 74073-74954 | 882 | |
| 6a | 74955-75118 | 164 | 6a | 75119-76254 | 1136 | |
| 6b | 76255-76380 | 126 | 6b | 76381-79806 | 3426 | |
| 7 | 79807-80053 | 247 | 7 | 80054-81722 | 1669 | |
| 8 | 81723-81815 | 93 | 8 | 81816-88347 | 6532 | |
| 9 | 88348-88530 | 183 | 9 | 88531-99170 | 10640 | |
| 10 | 99171-99362 | 192 | 10 | 99363-127445 | 28083 | |
| 11 | 127446-127540 | 95 | 11 | 127541-130059 | 2519 | |
| 12 | 130060-130146 | 87 | 12 | 130147-131640 | 1494 | |
| 13 | 131641-132364 | 724 | 13 | 132365-134636 | 2272 | |
| 14a | 134637-134765 | 129 | 14a | 134766-142532 | 7767 | |
| 14b | 142533-142570 | 38 | 14b | 142571-173238 | 30668 | |
| 15 | 143239-143489 | 251 | 15 | 143490-146380 | 2891 | |
| 16 | 146381-146460 | 80 | 16 | GenBannk AC000111 (146461-149354) + Genbank AC000061 (1-871) | 3765 | |

FIG. 1 (continued)

| Exon | Location on Corresponding Genbank | Length in bp | IVS | Location on Corresponding Genbank | Length in bp | |
|---|---|---|---|---|---|---|
| 17a | 872-1022 | 151 | 17a | 1023-1933 | 911 | GenBank #AC000061 |
| 17b | 1934-2161 | 228 | 17b | 2162-4965 | 2804 | |
| 18 | 4966-5066 | 101 | 18 | 5067-17874 | 12808 | |
| 19 | 17875-18123 | 249 | 19 | 18124-32790 | 14667 | |
| 20 | 32791-32946 | 156 | 20 | 32947-43194 | 10248 | |
| 21 | 43195-43284 | 90 | 21 | 43285-55040 | 11756 | |
| 22 | 55041-55213 | 173 | 22 | 55214-55811 | 598 | |
| 23 | 55812-55917 | 106 | 23 | 55918-57260 | 1343 | |
| 24 | 57261-59014 | 1754 | | | | |

SEQUENCE LISTING

```
<160> NUMBER OF SEQ ID NOS: 90

<210> SEQ ID NO 1
<211> LENGTH: 8
<212> TYPE: PRT
```

<213> ORGANISM: Homo sapiens

<400> SEQUENCE: 1

Arg Ser Glu Ser Trp Glu Asp Glu
1 5

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
catggtgggc ccggccta 18

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
gagcatggtg ggcccggcct aaaa 24

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
gtgtagtgag catggtgggc ccggcctaaa aaatactt 38

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
actgtcgccc acctgcgg 18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ccgcacacca ccccttcc 18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
aattggaagc aaatgacatc acag 24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ttcctttacc ccaaacccaa 20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cctctcttta ttttagctgg accagac 27

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tcaactaaac aatgtacatg aacatacct 29

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gaatgggata gagagctggc t 21

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tgtacaaatg agatccttac cccta 25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gaagtcacca aagcagtaca gcc 23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gcctgtgcaa ggaagtatta cct 23

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tttagacttt aaagctgtca agccg 25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ccgcctttcc agttgtataa tttat 25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggacttgcat tggcacattt 20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tgctacctgt acttcatcat cattc 25

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tgtaaaacga cggccagtag atcagagagc tgggaagatc a 41

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ggtggaagtc taccatgata aacat 25

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aacagaactg aaactgactc gga 23

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcagcattat ggtacattac ctgta 25

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tttttttttt tttttataag atgtagcaca atgagagtat aaagt 45

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
taaaaattct gacctcctcc ca 22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tggatcatgg gccatgtgc 19

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
caaaagaact accttgcctg ct 22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tccagacttc acttctaatg gtga 24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
gtgaagggtt catatgcata atcaa 25

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
aggacatctc caagtttgca ga 22

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gcaaatgctt gctagaccaa taatt 25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tgaccaggaa atagagagga aatg 24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ctatgatggg acagtctgtc tttct 25

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gtgatcagca ctggccccac 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cccccaagcg atgtatacct 20

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ttttgagtgc ttttttgatg atatggaga 29

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
aacattctta cctctgccag aaaa 24

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ggaggaatag gtgaagatgt tagaa 25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ggagaaatga aacaaagtgg attac 25

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ttttttttca ctcctcttca agacaaaggg 30

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
tacctgcttt caacgtgttg ag 22

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gcgtctactg tgatccaaac ttagt 25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ggacttcaac cctcaatcaa ataaa 25

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ttctcaccaa catgttttct ttgatc 26

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gtcatacctt cagattccag ttgtt 25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tggaaatatt tcacaggcag gagtc 25

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
cattttattc attgaaaatt ttttacttaa atg 33

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tacttactat atgcagagca ttattctatt agtag 35

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cttaccaagc tatccacatc tatgc 25

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
atgcgatctg tgagccgagt 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ccctctggcc aggacttatt 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gtgggcctct tgggaagaac 20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gctcacctgt ggtatcactc caa 23

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tgtaaaacga cggccagtct tttctttttt gctatagaaa gtatttattt t 51

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cagccttacc tcatctgcaa ctt 23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gttgggctca gatctgtgat aga 23

<210> SEQ ID NO 56

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
cacactggat ccaaatgagc ac 22

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cattactgtt ctgtgatatt atgtgtggta 30

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
caagggcaat gagatcttaa gtaa 24

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
agaagagaac aaagtgcggc a 21

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tgtatcttgc acctcttctt ctgtc 25

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 61 ttttttttt tgtaaaacga cggccagttt cagtctttac tgaaattaaa aaatctt 57

<210> SEQ ID NO 62
<211> LENGTH: 26

<212> TYPE: DNA
<213> ORGANISM: Artificial Sequence
<220> FEATURE:
<223> OTHER INFORMATION: Description of Artificial Sequence: Synthetic primer

<400> SEQUENCE: 62
atagcatacg gtttctagag gacatg 26

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ttgaaggaaa tgccccatta tttagccagg 30

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tgcttaacaa gaccatacta cagtgacgt 29

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
aggaggacct gtcctcccag atggt 25

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ctgtccagcc aggagacccc a 21

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
cattcttacc tggtccccag gacaaag 27

<210> SEQ ID NO 68
<211> LENGTH: 25
<212> TYPE: DNA

<213> ORGANISM: Artificial Sequence
<220> FEATURE:
<223> OTHER INFORMATION: Description of Artificial Sequence: Synthetic primer

<400> SEQUENCE: 68
gtcctacaac cctgtcaccc acatc 25

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gaattcaaag gaaaacataa gatgcaattc 30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
aacacacatt acagtcttac aaagatgttt 30

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ccacactaac agttataaac caaacaaca 29

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
caccaggaaa gaatttcagc attt 24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ctaaaacact ccaaagcctt cctt 24

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ttcaggttta ggtgagtgaa ctccaa 26

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tgtaaaacga cggccagtaa agtcttgtgt tgaaattctc agg 43

<210> SEQ ID NO 76
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
caggaaacag ctatgaccca gctcactacc taatttatga cat 43

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
tgtaaaacga cggccagtct tccattccaa gatccc 36

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
caggaaacag ctatgaccgc aaagttcatt agaactgatc 40

<210> SEQ ID NO 79
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
tgtaaaacga cggccagttg gatcatgggc catgtgc 37

<210> SEQ ID NO 80
<211> LENGTH: 43
<212> TYPE: DNA
<213> ORGANISM: Artificial Sequence
<220> FEATURE:

<223> OTHER INFORMATION: Description of Artificial Sequence: Synthetic primer

<400> SEQUENCE: 80
caggaaacag ctatgaccaa agagacatgg acaccaaatt aag 43

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
tgtaaaacga cggccagtag cagagtacct gaaacagga 39

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
caggaaacag ctatgaccca ttcacagtag cttaccca 38

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
tgtaaaacga cggccagtgg ttaagggtgc atgctcttc 39

<210> SEQ ID NO 84
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
caggaaacag ctatgaccgg ccctattgat ggtggatc 38

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
tgtaaaacga cggccagtac actttgtcca ctttgc 36

<210> SEQ ID NO 86
<211> LENGTH: 37
<212> TYPE: DNA
<213> ORGANISM: Artificial Sequence
<220> FEATURE:
<223> OTHER INFORMATION: Description of Artificial Sequence: Synthetic

```
      primer

<400> SEQUENCE: 86

caggaaacag ctatgaccag atgagtatcg cacattc                              37


<210> SEQ ID NO 87
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

tgtaaaacga cggccagtat ctattcaaag aatggcac                             38


<210> SEQ ID NO 88
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

caggaaacag ctatgaccga taacctatag aatgcagc                             38


<210> SEQ ID NO 89
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

tgtaaaacga cggccagtag cagagtacct gaaacagga                            39


<210> SEQ ID NO 90
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

caggaaacag ctatgaccgt ggaagtctac catgataaac ata                       43
```

CYSTIC FIBROSIS TRANSMEMBRANE CONDUCTANCE REGULATOR GENE MUTATIONS

CROSS-REFERENCE TO RELATED APPLICATIONS

This application is a continuation of U.S. patent application Ser. No. 15/222,218, filed Jul. 28, 2016, now U.S. Pat. No. 9,863,000, which is a continuation of U.S. patent application Ser. No. 12/909,141, filed Oct. 21, 2010, now U.S. Pat. No. 9,422,606, which is a continuation of U.S. patent application Ser. No. 11/506,453, filed Aug. 18, 2006, now U.S. Pat. No. 7,838,646 which claims priority under 35 USC § 119 (e) to U.S. Provisional Patent Application No. 60/709,329 filed Aug. 18, 2005, the entire contents of which are incorporated by reference herein.

BACKGROUND OF THE INVENTION

The following description of the background of the invention is provided simply as an aid in understanding the invention and is not admitted to describe or constitute prior art to the invention.

The present invention relates to a novel cystic fibrosis transmembrane regulator (CFTR) gene mutation and its use in the diagnosis of cystic fibrosis. Cystic fibrosis (CF) is the most common severe autosomal recessive genetic disorder in the Caucasian population. It affects approximately 1 in 2,500 live births in North America (Boat et al, The Metabolic Basis of Inherited Disease, 6th ed, pp 2649-2680, McGraw Hill, NY (1989)). Approximately 1 in 25 persons are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). There are greater than 1,000 different mutations in the CFTR gene, having varying frequencies of occurrence in the population, presently reported to the Cystic Fibrosis Genetic Analysis Consortium. These mutations exist in both the coding regions (e.g., ΔF508, a mutation found on about 70% of CF alleles, represents a deletion of a phenylalanine at residue 508) and the non-coding regions (e.g., the 5T, 7T, and 9T mutations correspond to a sequence of 5, 7, or 9 thymidine bases located at the splice branch/acceptor site of intron 8) of the CFTR gene. Comparison of the CFTR genomic and cDNA sequences confirms the presence of 27 exons. The exons are numbered 1, 2, 3, 4, 5, 6a, 6b, 7, 8, 9, 10, 11, 12, 13, 14a, 14b, 15, 16, 17a, 17b, 18, 19, 20, 21, 22, 23, and 24. Each intron is flanked by the consensus GT-AG splice-site sequence as previously reported (Zielenski, et al., (1991) Genomics 10, 214-228).

The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

Methods for detecting CFTR gene mutations have been described. See e.g., Audrezet et al., "Genomic rearrangements in the CFTR gene: extensive allelic heterogeneity and diverse mutational mechanisms" Hum Mutat. 2004 April; 23(4):343-57; PCT WO 1004/040013 A1 and corresponding US application #20040110138; titled "Method for the detection of multiple genetic targets" by Spiegelman and Lem; US patent application No. 20030235834; titled "Approaches to identify cystic fibrosis" by Dunlop et al.; and US patent application No. 20040126760 titled "Novel compositions and methods for carrying out multiple PCR reactions on a single sample" by N. Broude.

A variety of CFTR gene mutations are known, and the identification of additional mutations will further assist in the diagnosis of cystic fibrosis.

SUMMARY OF THE INVENTION

The inventors have discovered a new mutation in the CFTR gene that results in a duplication of exons 6b through 10 and leads to cystic fibrosis or is associated with conditions associated with cystic fibrosis. By "conditions associated with cystic fibrosis" is meant any clinical symptoms that may be found in a cystic fibrosis patient and are due to one or more CF mutations.

In a one embodiment, the duplicated segment containing exons 6b-10 represents about 26,817 base pairs (bp). In another embodiment, the duplicated segment is 26,817 base pairs, defined as gIVS6a+415_IVS10+2987Dup26817 bp in accordance with guidelines from the Human Genome Variation Society. The duplicated 26,817 bp segment begins at position 415 of the CFTR intron 6a and ends at position 2987 of the CFTR intron 10. The duplicated region is inserted between IVS10+2,987 and IVS10+2,988 and which results in a unique junction IVS10+2,987/IVS6a+415. The term "IVS6a+415" is a shorthand identifier for position 415 measured from the start of intron 6a, while the term "IVS10+2,987" is a shorthand identifier for position nucleotide position 2,987 measured from the start of intron 10. The term "Dup ex 6b-10" is used herein as a shorthand for gIVS6a+415_IVS10+2987Dup26817 bp. The nucleotide positions of the exons and introns for the human CFTR gene is shown in FIG. 1.

The unique junctions generated by duplications of exon 6b-10 generates new amino new sequence. For example, Dup ex 6b-10 of the CFTR gene results in an out-of-frame addition of 8 amino acids after codon E528 of exon 10, encoding a new C-terminal sequence between 529 and 536 (Arg-Ser-Glu-Ser-Trp-Glu-Asp-Glu; SEQ ID NO:1), followed by a TGA Stop codon. The result is a truncated CFTR protein lacking the terminal NBD1 domain and beyond and having an 8 mer non-CFTR gene C-terminal far end sequence (SEQ ID NO:1). Dup ex 6b-10 of the CFTR gene causes early truncation of the protein product, resulting in a nonfunctional CFTR protein.

The present invention provides a method of detecting if a CFTR gene in nucleic acid from an individual has a duplication of exons 6b through 10 by detecting the duplication of at least one portion of exons 6b through 10.

The present invention also provides a method of screening a subject to determine if the subject is a CF carrier or a CF patient, the method comprising determining if a CFTR gene in nucleic acid from the individual has a duplication of exons 6b through 10 by detecting the duplication of at least one portion of exons 6b through 10.

The present invention further provides a method of determining if an individual is predisposed to cystic fibrosis or a condition associated with cystic fibrosis, the method comprising determining if a CFTR gene in nucleic acid from the individual has a duplication of exons 6b through 10 by detecting the duplication of at least one portion of exons 6b through 10.

The present invention still further provides a method of counseling an individual on the likelihood of having an offspring afflicted with cystic fibrosis or a condition associated with cystic fibrosis, the method comprising determining if a CFTR gene in nucleic acid from the individual has a duplication of exons 6b through 10 by detecting the duplication of at least one portion of exons 6b through 10.

In any of above methods, a sequence from the CFTR gene may be amplified and the amplified sequence tested for the presence of the duplication. In a preferred approach, amplification is by the polymerase chain reaction.

In another embodiment, the exon 6b-10 duplication of the CFTR gene is detected by (a) amplifying sequence from one or more of exon 6b, 7, 8, 9, and 10 from nucleic acid from the individual; (b) identifying the amplified exon sequence; and (c) comparing the amount of each amplified exon sequence versus that similarly amplified for a normal CFTR gene, wherein a substantial increase in the amount of amplified exon sequence observed versus that for a normal CFTR gene indicates a duplication of exon 6b-10. The exon sequence is preferably amplified using oligonucleotide primer pairs that hybridize upstream and downstream of the exon sequence to be amplified. Preferably, sequence from most or all of exons 6b, 7, 8, 9, and 10 are amplified and evaluated. The exon sequence may be amplified using primers specific to intron or exon sequence. Sequence may be amplified from introns instead of or in addition to sequence from the corresponding exon and then used for comparison with that of a similarly amplified sequence from wildtype nucleic acid. If multiplex amplification is desired, one primer of each primer pair may be detectably labeled to allow discrimination of the different amplified products. In this method, amplification is preferably conducted in the linear phase (e.g. SQF PCR).

Sequence representing exons may be amplified using primers for one or more introns within the duplicated 6b-10 segment and compared to that similarly amplified from a normal gene. Sequence also may be amplified from introns instead of or in addition to sequence being amplified from exons.

In yet another embodiment, the exon 6b-10 duplication of the CFTR gene is detected by amplifying with primers that flank the unique junction formed between introns 10 and 6a created by the duplication. The forward primer is complementary to sequence upstream (3') of the junction while the reverse primer is complementary to sequence downstream of the junction. The distance between the forward and reverse primers are chosen to optimize the size of the product amplified or to achieve detection by a Real Time PCR method such as the TaqMan system. In another embodiment, the junction fragment is detected by agarose gel electrophoresis. In this embodiment, the size of the junction fragment can vary depending on where the forward and reverse primers that flank the duplication are placed. In mutations where the junction is IVS10+2,987:IVS6a+415, the forward primer is complementary to sequence upstream of IVS10+2987 and the reverse primer is complementary to sequence downstream of IVA6a+415. In a further embodiment, amplified product may be sequenced to verify the 6b-10 junction.

In a further embodiment, the exon 6b-10 duplication of the CFTR gene is detected using MLPA (i.e., multiplex ligation-dependent probe amplification) or MAPH (i.e., multiplex amplifiable probe hybridization).

In another embodiment, the exon 6b-10 duplication of the CFTR gene is detected by amplifying with primers that flank the 6b-10 segment. In one approach, a forward primer is used hybridizing to a segment preceding IVS6a+415 and a reverse primer is used hybridizing to a segment following IVS10+2987. Such analysis of a wild-type CFTR gene will amplify a product that includes 26,817 bp while a duplication of exons 6a through 10 in one allele will result in two fragments, one of which includes the 26,817 representing the single 6b-10 segment and a fragment which includes 53,634 bp containing the duplication (i.e. 6b-10-6b'-10'). By locating the primers close to IVS6a+415 and IVS10+2987, the resulting amplified products will approach the size of the target 6b-10 segment (26,817 bp) and the size of the 6b-10-6b'-10' segment (54,634 bp). For example, primers located very close to the specified sites will amplify from the normal CFTR gene a product of about 26,817 bp and from the CFTR gene with a Dup ex 6b-10 mutation, a product of about 53,634 bp.

The term "about" is used herein to refer to +/−5% of a given measurement unless otherwise indicated.

In any of the above embodiments where amplification is employed, RealTime PCR can be used to detect amplification of any exons, introns or segments thereof or the duplication junction created by the 6b-10 duplication of the CFTR gene. The positioning of the primers and the use of TaqMan system probes can be detected using an automated fluorescence detection device (e.g. Applied Biosystems 7900). In a different embodiment the duplication of exons 6b-10 can be detected using increase in signal and cycle threshold on the TaqMan system (or equivalent) after amplification of any one or more of exons 6b-10 or intron fragments and comparing to normal sample. In this embodiment the use of an internal control for signal normalization may or may not be utilized.

In a further embodiment, the exon 6b-10 duplication of the CFTR gene is detected by Southern Blot analysis.

In another embodiment, the exon 6b-10 duplication of the CFTR gene can be detected by detecting a unique protein C-terminal sequence that results from the duplication. For example, the Dup ex 6b-10 mutation is identified by detecting the C-terminal sequence Arg-Ser-Glu-Ser-Trp-Glu-Asp-Glu (SEQ ID NO:1) between 529 and 536 of the CFTR protein encoded by the CFTR gene with the Dup ex 6b-10 mutation. In one embodiment, an antibody specific for the CFTR product containing the unique C-terminal amino acid sequence (e.g. SEQ ID NO: 1) is used to detect the truncated CFTR protein in a sample from an individual. Specific binding of the antibody to the truncated CFTR gene product resulting from the exon 6b-10 duplication may be detected by ELISA, radioimmunoassay, and the like.

In any of the above methods, amplified product may be separated by size. In a further embodiment, size separation may be performed by gel electrophoresis. In yet a further embodiment, size separation may be performed by capillary electrophoresis.

In any of the above methods, at least one primer of each primer pair for amplification is detectably labeled with a detectable moiety.

Also provided herein are nucleic acid fragments containing the unique junction between exons 10 and 6b' that occur as a result of the exon 6b-10 duplication. The fragments are about 26 kb or less and include the intron 10 to intron 6a junction formed as a result of the exon 6b to 10 duplication of the CFTR gene. The junction includes a sequence with at least nine nucleotides directly adjoining each side of the junction. In one embodiment, the sequence with at least nine nucleotides directly adjoining each side of the junction is CATGGTGGG:CCCGGCCTA (SEQ ID NO: 2) (the junction between the intron 10 and intron 6a is depicted by the symbol ":"). In another embodiment, the sequence with at least nine nucleotides directly adjoining each side of the junction is GAGCATGGTGGG:CCCGGCCTAAAA (SEQ ID NO: 3). In yet another embodiment, the sequence with at least nine nucleotides directly adjoining each side of the junction is GTGTAGTGAGCATGGTGGG:CCCGGC-CTAAAAAATACTT (SEQ ID NO: 4).

In an embodiment, the detection can be accomplished by amplifying the junction fragment and performing restriction enzyme digestion that recognizes the junction sequence, e.g. ApaI which recognizes the sequence GGG:CCC. In a further embodiment, the detection of the duplication can be accomplished by analyzing using Arrays (exon arrays, SNP arrays, and the like) or by linkage analysis of variable polymorphic markers.

Other known CFTR mutations may be evaluated in nucleic acid samples along with that of the 6b-10 duplication are described in U.S. patent application Ser. No. 11/074,903 titled "Cystic Fibrosis Gene Mutations" and filed Mar. 7, 2005 and in U.S. Publication no. 20050059035 (Mar. 17, 2005) by Huang et al. These and other known mutations in the CFTR gene may be determined by any of a variety of well known methods used to detect single base changes (transitions and/or small deletions/insertions) or by any of a variety of well known methods used to detect exon duplication or deletion. Thus, genomic DNA may be isolated from the individual and tested for the CF mutations. In another approach, mRNA can be isolated and tested for the CF mutations. Testing may be performed on mRNA or on a cDNA copy.

Methods for amplifying multiple target segments of the CFTR gene in a single vessel using oligonucleotide primer pairs specific to each of the target segments in a multiplex polymerase chain reaction (PCR) can be used as described in U.S. patent Ser. No. 10/942,257 titled "Method of detecting cystic fibrosis" filed Sep. 16, 2004. This multiplex amplification, which can detect one or more or all of the 27 exons of the CFTR gene, may also include a primer pair for at least one internal control target segment of nucleic acid that does not correspond to the CFTR gene. In a preferred embodiment, the internal controls can be segments of various genes. Such segments can include an exon from the Tay Sachs HEXA gene, an exon from coagulation factor II gene and/or an exon from the coagulation factor V gene. Other internal controls can be used. Preferably, the internal controls reside on different chromosomes from the CFTR gene, or on the short arm of chromosome 7.

Following amplification, the various target segments are separately identified and evaluated for the relative amount of the segment present versus that for a control (i.e., wildtype) CFTR gene. In a preferred embodiment, the amplified segments are separated by size such as by gel electrophoresis and or by color.

A substantial increase in the amount of a CFTR target segment identified means that the segment has been duplicated while a substantial decrease in the amount of a CFTR target segment identified means that the target segment has been deleted. The term "substantial decrease" or "substantial increase" means a decrease or increase of at least about 30-50%. Thus, deletion of a single CFTR exon would appear in the assay as a signal representing for example of about 50% of the same exon signal from an identically processed sample from an individual with a wildtype CFTR gene. Conversely, amplification of a single exon would appear in the assay as a signal representing for example about 150% of the same exon signal from an identically processed sample from an individual with a wildtype CFTR gene.

In a preferred embodiment, at least one primer of each primer pair in the PCR is labeled with a detectable moiety. Thus, following amplification, the various target segments can be identified by size and color. The detectable moiety is preferably a fluorescent dye. In some embodiments, different pairs of primers in a multiplex PCR may be labeled with different distinguishable detectable moieties. Thus, for example, HEX and FAM fluorescent dyes may be present on different primers in the multiplex PCR and associated with the resulting amplicons. In other embodiments, the forward primer will be labeled with one detectable moiety, while the reverse primer will be labeled with a different detectable moiety, e.g. FAM dye for Forward primer and Hex due for Reverse primer. Use of different detectable moieties is useful for discriminating between amplified products which are of the same length or are very similar in length. Thus, in a preferred embodiment, at least two different fluorescent dyes are used to label different primers used in a single amplification. In still another embodiment, the normal (wt) control primers can be labeled with one moiety, while the patient (or test sample) primers can be labeled with a different moiety, to allow for mixing of both samples (post PCR) and the simultaneous detection and comparison of signals of normal and test sample. In a modification of this embodiment, the primers used for wt samples and patient samples can be switched to allow for further confirmation of results.

Analysis of amplified products from multiplex PCR reactions can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label.

In another aspect, the present invention provides kits for one of the methods described herein. In various embodiments, the kits contain one or more of the following components in an amount sufficient to perform a method on at least one sample: one or more primers of the present invention, one or more devices for performing the assay, which may include one or more probes that hybridize to a mutant CF nucleic acid sequence, and optionally contain buffers, enzymes, and reagents for performing a method of detecting a genotype of cystic fibrosis in a nucleic acid sample.

BRIEF DESCRIPTION OF THE FIGURES

FIG. 1 identifies the boundaries of the various exons and introns for the CFTR gene. This data for particular regions of the gene were obtained from GenBank using accession #s AC000111 and AC000061 as shown.

DETAILED DESCRIPTION OF THE INVENTION

Figure 2:
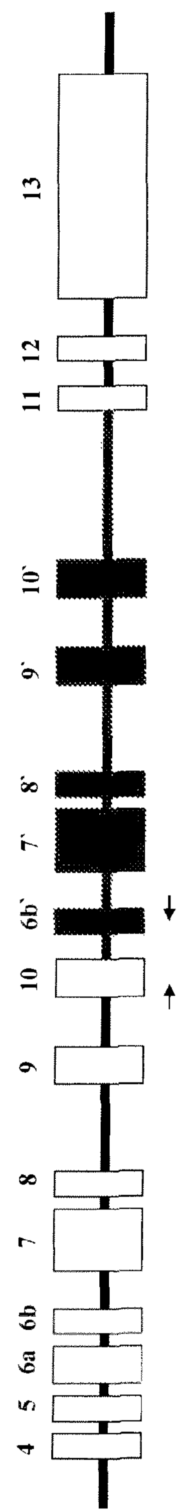
FIG. 2 is a schematic showing the CFTR gene structure for an individual with an exon 6b-10 duplication. The duplicated exons are identified 6b', 7', 8', 9' and 10'. The arrows indicate one location of PCR primers designed to amplify across the unique junction.

By the present invention, there are provided methods for detecting a mutation of the CFTR gene which is a duplication of exons 6b-10 and for using this information to assist in clinical diagnosis of CFTR disease or carrier status and for genetic consuling.

By "mutations of the CFTR gene" or "mutant CF sequence" is meant one or more CFTR nucleic acid sequences that are associated or correlated with cystic fibrosis. The nucleic acid sequences containing CF mutations are preferably DNA sequences, and are preferably genomic DNA sequences; however, RNA sequences such as mRNA or hnRNA may also contain nucleic acid mutant sequences that are associated with cystic fibrosis. The presence of CF mutations described herein can be determined in a nucleic acid by sequencing appropriate portions of the CFTR gene containing the mutations sought to be detected. In another approach, CF mutations that change susceptibility to digestion by one or more endonuclease restriction enzymes may be used to detect the mutations. Other mutation approaches include allele specific amplification, sequencing by primer extension, oligonucleotide ligation and specific hybridization. These methods are merely exemplary of those that can be used to detect CF mutations described herein.

By "carrier state" is meant a person who contains one CFTR allele that is a mutant CF nucleic acid sequence, but a second allele that is not a mutant CF nucleic acid sequence. CF is an "autosomal recessive" disease, meaning that a mutation produces little or no phenotypic effect when present in a heterozygous condition with a non-disease related allele, but produces a "disease state" when a person is homozygous, i.e., both CFTR alleles are mutant CF nucleic acid sequences. A carrier status is whether or not one is a carrier.

By "primer" is meant a sequence of nucleic acid, preferably DNA, that hybridizes to a substantially complementary target sequence and is recognized by DNA polymerase to begin DNA replication. The term primer as used herein includes all forms of primers that may be synthesized including peptide nucleic acid primers, locked nucleic acid primers, phosphorothioate modified primers, labeled primers, and the like.

By "substantially complementary" is meant that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

By "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase. Primers that flank mutant CF sequences do not actually anneal to the mutant sequence but rather anneal to sequence that adjoins the mutant sequence. In particular, primers that flank a CF exon are generally designed not to anneal to the exon sequence but rather to anneal to sequence that adjoins the exon (e.g. intron sequence). However, in some cases, amplification primer may be designed to anneal to the exon sequence.

By "isolated" a nucleic acid (e.g., an RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

By "crude" a nucleic acid represents at or less than 50% of a nucleic acid in a sample. Crude nucleic also encompasses nucleic acid in cell lysates. The nucleic acid sample may exist in solution or as a dry preparation.

By "substantially pure" a nucleic acid, represents more than 50% of the nucleic acid in a sample. The nucleic acid sample may exist in solution or as a dry preparation.

By "complement" and like words, e.g., "complementary" and "complementarity", is meant the complementary sequence to a nucleic acid according to standard Watson/Crick pairing rules. For example, a sequence 5'-GCGGTCCCA-3' has the complement 5'-TGGGACCGC-3'. A complement sequence can also be a sequence of RNA complementary to the DNA sequence or its complement sequence, and can also be a cDNA. Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Nucleic acid suspected of containing mutant CF sequences are amplified using one or more primers that flank the mutations under conditions such that the primers will amplify CFTR fragments containing the mutations, if present. The oligonucleotide sequences in Table 2 are useful for amplifying segments of the CFTR gene which contain the mutations in Table 1. Nucleic acid from an individual also could be tested for CFTR mutations other than those in Table 1.

The method of identifying the presence or absence of mutant CF sequence by amplification can be used to determine whether a subject has a genotype containing one or more nucleotide sequences correlated with cystic fibrosis. The presence of a wildtype or mutant sequence at each predetermined location can be ascertained by the invention methods.

By "amplification" is meant one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

Nucleic acid suspected of containing mutant CF sequence may be obtained from a biological sample. By "biological sample" is meant a sample obtained from a biological source. A biological sample can, by way of non-limiting example, consist of or comprise blood, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. The term biological sample includes samples which have been processed to release or otherwise make available a nucleic acid for detection as described herein. For example, a biological sample may include a cDNA that has been obtained by reverse transcription of RNA from cells in a biological sample. The biological sample may be obtained from a stage of life such as a fetus, young adult, adult, and the like. Fixed or frozen tissues also may be used. Whole blood samples of about 0.5 to 5 ml collected with EDTA, ACD or heparin as anti-coagulant are generally suitable. Amniotic fluid of 10-15 ml, cultured cells which are 80-100% confluent in two T-25 flasks and 25 mg of chorionic villi are useful sample amounts for processing.

By "subject" is meant a human or any other animal which contains as CFTR gene that can be amplified using the primers and methods described herein. A subject can be a patient, which refers to a human presenting to a medical provider for diagnosis or treatment of a disease. A human includes pre and post natal forms. Particularly preferred subjects are humans being tested for the existence of a CF carrier state or disease state.

By "identifying" with respect to an amplified sample is meant that the presence or absence of a particular nucleic acid amplification product is detected. Numerous methods for detecting the results of a nucleic acid amplification method are known to those of skill in the art.

The term "deletion" as used herein encompasses a mutation that removes one or more nucleotides from nucleic acid. Conversely, the term "duplication" refers to a mutation that inserts one or more nucleotides of identical sequence directly next to this sequence in the nucleic acid. In a preferred embodiment, a deletion or duplication involves a segment of four or more nucleotides.

The term "amplify" as used herein with respect to nucleic acid sequences, refers to methods that increase the representation of a population of nucleic acid sequences in a sample. Amplification may be exponential or linear. The sequences amplified in this manner form an "amplicon." In a preferred embodiment, the amplification by the is by the polymerase chain reaction ("PCR") (e.g., Mullis, K. et al., Cold Spring Harbor Symp. Quant. Biol. 51:263-273 (1986); Erlich H. et al., European Patent Appln. 50,424; European Patent Appln. 84,796, European Patent Application 258,017, European Patent Appln. 237,362; Mullis, K., European Patent Appln. 201,184; Mullis K. et al., U.S. Pat. No. 4,683,202; Erlich, H., U.S. Pat. No. 4,582,788; and Saiki, R. et al., U.S. Pat. No. 4,683,194). Other known nucleic acid amplification procedures that can be used include, for example, transcription-based amplification systems or isothermal amplification methods (Malek, L. T. et al., U.S. Pat. No. 5,130,238; Davey, C. et al., European Patent Application 329,822; Schuster et al., U.S. Pat. No. 5,169,766; Miller, H. I. et al., PCT appln. WO 89/06700; Kwoh, D. et al., Proc. Natl. Acad. Sci. (U.S.A.) 86:1173 (1989); Gingeras, T. R. et al., PCT application WO 88/10315; Walker, G. T. et al., Proc. Natl. Acad. Sci, (U.S.A.) 89:392-396 (1992)) Amplification may be performed to with relatively similar levels of each primer of a primer pair to generate an double stranded amplicon. However, asymmetric PCR may be used to amplify predominantly or exclusively a single stranded product as is well known in the art (e.g., Poddar et al. *Molec. And Cell. Probes* 14:25-32 (2000)). This can be achieved for each pair of primers by reducing the concentration of one primer significantly relative to the other primer of the pair (e.g. 100 fold difference). Amplification by asymmetric PCR is generally linear. One of ordinary skill in the art would know that there are many other useful methods that can be employed to amplify nucleic acid with the invention primers (e.g., isothermal methods, rolling circle methods, etc.), and that such methods may be used either in place of, or together with, PCR methods. Persons of ordinary skill in the art also will readily acknowledge that enzymes and reagents necessary for amplifying nucleic acid sequences through the polymerase chain reaction, and techniques and procedures for performing PCR, are well known. These various amplification methods are merely exemplary.

The phrase "comprise sequence from all or a portion of" in reference to an exon means that the sequence represents all of the exon or at least 10 bases of the exon. In other embodiments, most of the exon is amplified, generally greater than 50%, greater than 60%, greater than 70%, greater than 80%, greater than 90% and greater than 95%.

The term "specific" as used herein in reference to an oligonucleotide primer means that the hybridization sequence of the primer has at least 12 bases of sequence identity with a portion of the nucleic acid to be amplified when the oligonucleotide and the nucleic acid are aligned. An oligonucleotide primer that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "multiplex PCR" as used herein refers to amplification of two or more products which are each primed using a distinct primers pair.

The term "hybridize" or "specifically hybridize" as used herein refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "sense strand" as used herein means the strand of double-stranded DNA (dsDNA) that includes at least a portion of a coding sequence of a functional protein. "Anti-sense strand" means the strand of dsDNA that is the reverse complement of the sense strand.

The term "forward primer" as used herein means a primer that anneals to the anti-sense strand of dsDNA. A "reverse primer" anneals to the sense-strand of dsDNA.

The term "wildtype" as used herein with respect to the CFTR gene or a locus thereof refers to the CFTR gene sequence which is found in NCBI GenBank locus IDs M58478 (HUMCFTC), AC000111 and AC000061. The cDNA for the CFTR gene is found in Audrezet et al., Hum. Mutat. (2004) 23 (4), 343-357. Alleic variant is one that is "non-disease causing" and reaches a frequency of 1% or more in the population.

The term "familial history" as used herein means the individual has immediate family members including parents and siblings. Family history also may include grandparents.

Specific primers that aid in the detection of mutant CF genotype are disclosed. The sequence of substantially pure nucleic acid primers which are DNA (or an RNA equivalent) and which are useful for amplifying the promoter region, each of the 27 exons of the CFTR gene, an intronic sequence directly upstream of CFTR exon 9 and various exons of the internal control target segment are shown in Table 1. The letter F or R at the end of the primer name indicates whether the primer is a forward (F) or reverse (R) PCR primer. FAM and HEX refer to fluorescent compounds chemically linked to the 5' end of the oligonucleotide.

TABLE 1

CFTR Assay Primer Sequences

| SEQ ID NO | Primer Name | Sequence | Hybridizes to: |
|---|---|---|---|
| 5 | CFDELPF | 5'- 6-FAM/ACT GTC GCC CAC CTG CGG -3; | promoter |
| 6 | CFDELPR | 5'- CCG CAC ACC ACC CCT TCC -3' | promoter |
| 7 | CFDEL1F | 5'- 6-FAM/AAT TGG AAG CAA ATG ACA TCA CAG -3' | exon 1 |
| 8 | CFDEL1R | 5'- TTC CTT TAC CCC AAA CCC AA -3' | intron 1 |
| 9 | CFDEL2F | 5'-6-FAM/CCT CTC TTT ATT TTA GCT GGA CCA GAC -3' | intron 1/axon 2 |
| 10 | CFDEL2R | 5'- TCA ACT AAA CAA TGT ACA TGA ACA TAC CT -3' | exon 2/intron 2 |
| 11 | CFDEL3F2 | 5'-6-FAM/GAA TGG GAT AGA GAG CTG GCT -3' | exon 3 |
| 12 | CFDEL3R | 5'- TGT ACA AAT GAG ATC CTT ACC CCT A -3' | exon 3/intron 3 |
| 13 | CFDEL4F | 5'-6-FAM/GAA GTC ACC AAA GCA GTA CAG CC -3' | Exon 4 |
| 14 | CFDEL4R | 5'- GCC TGT GCA AGG AAG TAT TAC CT -3' | Exon 4/Intron 4 |
| 15 | CFDEL5F | 5'-6-FAM/TTT AGA CTT TAA AGC TGT CAA GCC G -3' | Intron 4/. Exon 5 |
| 16 | CFDEL5R | 5'- CCG CCT TTC CAG TTG TAT AAT TTA T -3' | Intron 5 |
| 17 | CFDEL6aF | 5'-6-FAM/GGA CTT GCA TTG GCA CAT TT -3' | Exon 6a |
| 18 | CFDEL6aR | 5'- TGC TAC CTG TAC TTC ATC ATC ATT C -3' | Exon 6a/Intron 6a |
| 19 | CFDEL6bF | 5'-6-FAM/TGT AAA ACG ACG GCC AGT AGA TCA GAG AGC TGG GAA GAT CA -3' | Exon 6b |
| 20 | CFDEL6bR | 5'- GGT GGA AGT CTA CCA TGA TAA ACA T -3' | Intron 6b |
| 21 | CFDEL7F | 5'-6-FAM/AAC AGA ACT GAA ACT GAC TCG GA -3' | Exon 7 |
| 22 | CFDEL7R | 5'- GCA GCA TTA TGG TAC ATT ACC TGT A -3' | Exon 7/Intron 7 |
| 23 | CFDELEX8F2 | 5'-6-FAM/TTT TTT TTT TTT TTT ATA AGA TGT AGC ACA ATG AGA GTA TAA AGT -3' | Intron 7 |
| 24 | CFDEL8R | 5'- TAA AAA TTC TGA CCT CCT CCC A -3' | exon 8/intron 8 |
| 25 | CFDELex9F2 | 5'-6-FAM/TGG ATC ATG GGC CAT GTG C -3' | Intron 8 |

TABLE 1-continued

CFTR Assay Primer Sequences

| SEQ ID NO | Primer Name | Sequence | Hybridizes to: |
|---|---|---|---|
| 26 | CFDEL9R | 5'- CAA AAG AAC TAC CTT GCC TGC T -3' | intron 9 |
| 27 | CFDEL10F | 5'-6-FAM/TCC AGA CTT CAC TTC TAA TGG TGA -3' | Intron 9/exon 10 |
| 28 | CFDEL10R | 5'- GTG AAG GGT TCA TAT GCA TAA TCA A -3' | intron 10 |
| 29 | CFDEL11F | 5'-6-FAM/AGG ACA TCT CCA AGT TTG CAG A -3' | intron 10/exon 11 |
| 30 | CFDEL11R | 5'- GCA AAT GCT TGC TAG ACC AAT AAT T -3' | intron 11 |
| 31 | CFDEL12F | 5'-6-FAM/TGA CCA GGA AAT AGA GAG GAA ATG -3' | intron 11 |
| 32 | CFDEL12R | 5'- CTA TGA TGG GAC AGT CTG TCT TTC T -3' | intron 12 |
| 33 | CFDEL13F | 5'-6-FAM/GTG ATC AGC ACT GGC CCC AC -3' | Exon 13 |
| 34 | CFDEL13R | 5'- CCC CCA AGC GAT GTA TAC CT -3' | Intron 13 |
| 35 | CFDEL14aF | 5'-6-FAM/TTT TGA GTG CTT TTT TGA TGA TAT GGA GA -3' | Exon 14a |
| 36 | CFDEL14aR | 5'- AAC ATT CTT ACC TCT GCC AGA AAA -3' | Exon 14a/intron 14a |
| 37 | CFDEL14bF | 5'-6-FAM/GGA GGA ATA GGT GAA GAT GTT AGA A -3' | Intron 14a |
| 38 | CFDEL14bR | 5'- GGA GAA ATG AAA CAA AGT GGA TTA C -3' | Intron 14b |
| 39 | CFDELI5F | 5'-6-FAM/TTT TTT TTC ACT CCT CTT CAA GAC AAA GGG -3' | Exon 15 |
| 40 | CFDEL15R | 5'- TAC CTG CTT TCA ACG TGT TGA G -3' | Exon 15/Intron 15 |
| 41 | CFDEL16F | 5'-6-FAM/GCG TCT ACT GTG ATC CAA ACT TAG T -3' | Intron 15 |
| 42 | CFDEL16R | 5'- GGA CTT CAA CCC TCA ATC AAA TAA A -3' | Intron 16 |
| 43 | CFDEL17aF | 5'- 6-FAM/TTC TCA CCA ACA TGT TTT CTT TGA TC -3' | Intron 16 |
| 44 | CFDEL17aR | 5'- GTC ATA CCT TCA GAT TCC AGT TGT T -3' | Exon 17a/Intron 17a |
| 45 | CFDEL17bF2 | 5'-6-FAM/TGG AAA TAT TTC ACA GGC AGG AGT C -3' | intron 17a/exon 17b |
| 46 | CFDEL17BR2 | 5'- CAT TTT ATT CAT TGA AAA TTT TTT ACT TAA ATG -3' | intron 17b |
| 47 | CFDEL18F2 | 5'-6-FAM/TAC TTA CTA TAT GCA GAG CAT TAT TCT ATT AGT AG -3' | Intron 17b |
| 48 | CFDEL18R | 5'- CTT ACC AAG CTA TCC ACA TCT ATG C -3' | Exon 18/Intron 18 |
| 49 | CFDEL19F | 5'-6-FAM/ATG CGA TCT GTG AGC CGA GT -3' | Exon 19 |
| 50 | CFDEL19R | 5'- CCC TCT GGC CAG GAC TTA TT -3' | Exon 19/Intron 19 |
| 51 | CFDEL20F | 5'-6-FAM/GTG GGC CTC TTG GGA AGA AC -3' | Exon 20 |
| 52 | CFDEL20R | 5'- GCT CAC CTG TGG TAT CAC TCC AA -3' | Exon 20/Intron 20 |
| 53 | CFDEL21F | 5'-6-FAM/TGT AAA ACG ACG GCC AGT CTT TTC TTT TTT GCT ATA GAA AGT ATT TAT TTT -3' | intron 20/exon 21 |
| 54 | CFDEL21R | 5'- CAG CCT TAC CTC ATC TGC AAC TT -3' | exon 21/intron 21 |
| 55 | CFDEL22F | 5'-6-FAM/GTT GGG CTC AGA TCT GTG ATA GA -3' | exon 22 |
| 56 | CFDEL22R | 5'- CAC ACT GGA TCC AAA TGA GCA C -3' | exon 22/intron 22 |
| 57 | CFDEL23F | 5'-6-FAM/CAT TAC TGT TCT GTG ATA TTA TGT GTG GTA -3' | intron 22 |
| 58 | CFDEL23R | 5'- CAA GGG CAA TGA GAT CTT AAG TAA -3' | intron 23 |
| 59 | CFDEL24F | 5'-6-FAM/AGA AGA GAA CAA AGT GCG GCA -3' | Exon 24 |
| 60 | CFDEL24R | 5'- TGT ATC TTG CAC CTC TTC TTC TGT C -3' | Exon 24 |
| 61 | Upex9F | 5'- /5HEX/TTT TTT TTT TTG TAA AAC GAC GGC CAG | Intron 8 |

TABLE 1-continued

CFTR Assay Primer Sequences

| SEQ ID NO | Primer Name | Sequence | Hybridizes to: |
|---|---|---|---|
| | | TTT CAG TCT TTA CTG AAA TTA AAA AAT CTT -3' | |
| 62 | Upex9R | 5'- ATA GCA TAC GGT TTC TAG AGG ACA TG -3' | Intron 8 |
| 63 | F5F | 5' - HEX/TTG AAG GAA ATG CCC CAT TAT TTA GCC AGG - 3' | Intron 11 |
| 64 | F5R | 5' - TGC TTA ACA AGA CCA TAC TAC AGT GAC GT - 3' | Exon 10 |
| 65 | F2F | 5' - 6-FAM/AGG AGG ACC TGT CCT CCC AGA TGG T -3' | Sequence Upstream of exon 1 |
| 66 | F2R | 5' - CTG TCC AGC CAG GAG ACC CCA -3' | Intron 1 |
| 67 | TSF | 5' - HEX/CAT TCT TAC CTG GTC CCC AGG ACA AAG -3' | Exon 7/Intron 8 |
| 68 | TSR | 5' - GTC CTA CAA CCC TGT CAC CCA CAT C -3' | Exon 7 |

Various subsets of the primer pairs from Table 1 may be used in a multiplex PCR. For example, primer sequences can be used to verify a suspected CFTR promoter deletion or duplication and to asses the extent of such deletion or duplication. Primer pairs which can be used to amplify three regions upstream from the promoter (Table 3) designated as UPr1, UPr2 and UPr3, are shown in Table 2. These may be combined in a multiplex amplification with primer pairs for CFTR exons 1, 2, 3 and 4 and/or others. In addition, one may include any number of internal control primer pairs.

TABLE 2

CFTR promoter and internal control primer concentrations in Master Mix

| SEQ ID NO: | Primer Name | Primer Sequence |
|---|---|---|
| 69 | UpPr1F | FAM-5'- GAA TTC AAA GGA AAA CAT AAG ATG CAA TTC -3' |
| 70 | UpPr1R | 5'- AAC ACA CAT TAC ACT CTT ACA AAG ATG TTT -3' |
| 71 | UpPr2F1 | FAM-5' - CCA CAC TAA CAG TTA TAA ACC AAA CAA CA -3' |
| 72 | UpPr2R | 5' - CAC CAG GAA AGA ATT TCA GCA TTT -3' |
| 73 | UpPr3F | FAM-5' - CTA AAA CAC TCC AAA GCC TTC CTT -3' |
| 74 | UpPr3R | 5' - TTC AGG TTT AGG TGA GTG AAC TCC AA- 3' |

Amplified target segments can be efficiently evaluated by size and/or detectable moiety using commercially available automated systems. For example, ABI PRISM® 3100 Genetic Analyzer can be used with an ABI PRISM 3100 capillary array, 36-cm (P/N#4315931). This provides a multi-color fluorescence-based DNA analysis system that uses capillary electrophoresis (CE) with 16 capillaries operating in parallel to separate labeled PCR products. A CE DNA sequencer/analyzer that operates 96 capillaries may be preferable in assays wherein 96-well plates are used. Analyzers with the capacity to process 96 wells include the MegaBACE™ 1000 DNA Analysis System (Molecular Dynamics, Inc and Amersham Pharmacia Biotech) and the 3700 DNA Analyzer from (Perkin-Elmer Biosystems).

The primers in Table 1 and 2 are useful for diagnosing a genetic basis for cystic fibrosis (CF) by analyzing a sample comprising nucleic acids from an individual. The method includes determining if the promoter region of the CFTR gene contains deleted or duplicated sequence involving four or more nucleotides, wherein the promoter region represents 250 nucleotides or more directly upstream of the CFTR start codon. These promoter/exon mutations include a deletion in a segment of the CFTR promoter region including the adjoining CFTR exon 1 or a deletion in a segment of the CFTR promoter region including the adjoining CFTR exons 1 and 2. The deletion involving the promoter region and exon 1 comprises at least 1,800 nucleotides in length of which at least 1,630 nucleotides represents sequence from the CFTR promoter region. The deletion involving the promoter and exons 1 and 2 comprises at least 28,000 nucleotides in length of which at least 3,570 nucleotides represents sequence from the CFTR promoter region. These deletions may be detected using the methods disclosed herein or other methods of deletion detection well known in the art.

Another method for detecting CF mutations is SQF PCR (i.e., semi-quantitative fluorescent multiplex PCR). This method also may be referred to as QMPSF (quantitative multiplex PCR of short fragments). See Bombieri et al, Eur J Human Genetics 13(5):687-9 (May 2005). A related approach is described by Yau and co-workers (Yau, S. C., et al., 1996, *J. Med. Genet.* 33:550-8). The principle of the method rests on comparisons of the fluorescent profiles of multiplex PCR fragments obtained from different samples, the amplification being stopped at the exponential phase. This procedure allows the detection of heterozygous deletions (i.e., approximately twofold reduction of fluoroescence intensity) and heterozygous duplications (i.e., approximately 1.5-fold increase in fluoroescence intensity). SQF PCR for simultaneous detection of deletions or duplications involving any of the 27 exons and the promoter of the CFTR gene is described in U.S. patent application Ser. No. 11/074,903 titled "Cystic Fibrosis Gene Mutations" and filed Mar. 7, 2005. Fragments representing any of the 27 CFTR exons can be amplified using the primers of Table 1 and operational protocols known to those of skill in the art. At the end of PCR cycling, the fluorescent PCR products are heat denatured, chilled on ice, and separated on a multi-capillary sequencer, e.g., ABI PRISM 3100 from Applied Biosystems. The resulting electropherograms are analyzed (manufacturer's Genescan software) to provide identification of product by size and to obtain correlated fluorescence intensity.

In the context of the exon 6b-10 duplication, one can use primers from Table 1 to (a) amplify sequence from one or more of exon 6b, 7, 8, 9, and 10 from nucleic acid from an individual; (b) identify the amplified exon sequence; and (c) compare the amount of each amplified exon sequence versus that for a normal CFTR gene, wherein a substantial increase in the amount of amplified exon sequence observed versus that for a normal CFTR gene indicates a duplication of exon 6b-10. In this approach, amplification is conducted in the linear phase in accordance with SQF PCR. Sequence representing exons may be amplified using primers for one or more introns within the duplicated 6b-10 segment and compared to that similarly amplified from a normal gene. Sequence also may be amplified from introns instead of or in addition to sequence being amplified from exons. If multiplex amplification is used, one primer of each primer pair may be detectably labeled to allow discrimination of the different amplified products.

An additional method of identifying CF mutations is MLPA (i.e., multiplex ligation-dependent probe amplification.). As known by those of skill in the art, MLPA is a sensitive technique enabling relative quantification of up to about 40 different nucleic acid sequences in one reaction (Schouten, J. P., et al., 2002, *Nucleic Acid Research* 30:e57; Sellner and Taylor, 2004 *Human Mutation* 23: 413-419). The method is based on adjacent hybridizing probes that if properly are hybridized, can be ligated together and then amplified using a specific primer pair. If a mutation is present, then a different adjoining probe will hybridize, be ligated and then amplified. The size of the amplified product will reveal the identify of the ligated probes. The amplified products also may be discriminated using size and/or differential labeling (e.g. different fluorescent molecules).

In the present context, appropriate probes and primers can be readily designed for detecting the 6b-10 duplication described herein or for detecting other CFTR deletions or duplications. For example, the two adjoining probes for the normal CFTR allele would be designed to hybridize so that ligation would occur between IVS10+2197 and IVS10+2198. In the case of the 6b-10 duplicated allele, the two adjoining probes would be designed to hybridize so that ligation would occur between IVS10+2197 and IVS6a+415.

A further method of identifying CF mutations is MAPH (i.e., multiplex amplifiable probe hybridization). See generally White et al. 2002, *Amer. J. Human Genetics,* 71:365-374; Sellner and Taylor, 2004. *Human Mutation.* 23: 413-419. As known by those of skill in the art, MAPH is based on a quantitative PCR of short DNA probes recovered after hybridization to a target of interest in immobilized genomic DNA. The target of interest is cloned into a vector and the probes are made by PCR using primers that flank the target sequence in the vector. In this way, the generated primers can have a known 5' primer site for subsequent PCR. The probes that hybridize to genomic DNA following appropriate stringent washing are removed and their identity determined by PCR using primers to the 5' primer sites. A universal 5' primer site can be incorporated into both forward and reverse primers along with appropriate stuffer sequence to obtain multiplex amplification of the bound probe and discrimination of amplicans by size. Probes directed to portions of the various exons of the CFTR gene are useful for MAPH. Duplications or deletions in genomic DNA show up as more or less probe binding, respectively in the MAPH method. Thus, typical CFTR exon probes for any or all of exon 6b, 7, 8, 9 and 10 can be used for detecting the 6b-10 CFTR exon duplication. One can also design a specific probe for MAPH by that spans the junction of fusion of IVs 10 to IVS6a.

An additional method of identifying CF mutations is long range PCR, which as known by those of skill in the art allows the amplification of PCR products which are much larger than those achieved with conventional Taq polymerases. In this regard, the present invention contemplates use of primers that flank the duplicated segment. Examples of such primers that flank the duplicated segment include any sequence preceding IVS6a+415 and any primer sequence which follows IVS10+2987. Such analysis of wild-type CFTR gene will amplify a product that includes 26,817 bp while a duplication of exons 6a through 10 in one allele will result in two fragments, one of which includes the 26,817 representing the single 6b-10 segment and a fragment including 53,634 bp which includes the double version of 6b-10. By placing the primers close to IVS6a+415 and IVS10+2987, the resulting amplified products will approach the size of the target 6b-10 segment (26,817 bp) and 6b-10-6b'-10' (54,634 bp).

Yet another method of identifying CF mutations is junction PCR. In the context of the exon 6b-10 duplication, primers are employed that flank the fusion of intron 10 and intron 6a in the mutant allele. Primers for this purpose, design of which is understood by those of skill in the art, would complement CFTR DNA upstream from IVS10+2987 (forward primer) and downstream of IVA6a+415 (reverse primer). The amplification of the junction encompassed by the primer would be confirmation of duplication, and DNA sequencing of the amplified junction fragment may be used to show the duplication junction. Restriction digestion of the amplified junction fragment using the enzyme ApaI or others that recognize the junction fragment can also be used as a confirmation.

An additional method of identifying CF mutations is RealTime PCR. In the context of the exon 6b-10 duplication, primers can be used that flank the intron 10/intron 6a junction of the mutant sequence are easily designed by those of skill in the art, are employed to amplify and detect the junction on a realtime instruction, e.g., the Applied Biosystems 7900, using TaqMan probes or equivalents.

In an additional method of identification of CFTR mutations including the exon 6b-10 duplication is Southern Blot analysis, well known to those of skill in the art. In this method, DNA is digested into fragments, preferably with a restriction endonuclease and the fragments separated by size via gel electrophoresis using, for example, agarose as the medium. To the developed DNA laden gel is pressed a nitrocellulose or nylon membrane to which the DNA sticks. The transferred DNA is then permanently fixed to the membrane by any of several methods, including for example, exposure to ultraviolet light or heat. The identity of the transferred DNA fragments is then determined by probing with complementary DNA probes which are labeled by any of several strategies including, for example, radioactivity, chromophoric, fluorophoric, or specific ligand including, for example, biotinylation. Visualization of probe bound to complementary DNA affixed to the membrane can occur based on the labeling method of the probe; for example, X-ray photographic exposure can revealed radioactive labeled probe, and fluoroescent labeling can be revealed by illumination with an exciting source and observation of the corresponding emitted signal. In application to detection of the CFTR 6b-10 duplication, enzymes that digest DNA outside exons 6b-10 can be used to detect the native 6b-10 segment (26,817 bp) and the duplicated segment 6b-10-6b'-10' (53,634 bp). In another application, digestion of the DNA with restriction enzymes (e.g. ApaI) that identify the junction fragment can help in identifying the exon 6b-10 duplication.

In a further method of identification of the CFTR 6b-10 exon duplication, the unique protein sequence that occurs as a result of the duplication may be detected. In a preferred approach, antibodies that specifically react with the unique protein segment are used to detect the 6b-10 duplication. For example, in the case of Dup ex 6b-10, there is an out-of-frame addition of 8 amino acids after codon E528 of Exon 10, encoding a new C-terminal sequence between 529 and 536 (Arg-Ser-Glu-Ser-Trp-Glu-Asp-Glu; SEQ ID NO: 1). Antibody binding specifically to a truncated CFTR protein via its unique C terminal segment such as that of SEQ ID NO:1 may be detected by any methods known in the art, including, for example, ELISA, radioimmunoassay, and western blotting.

Antibodies may be detectably labeled by methods known in the art. Labels include, but are not limited to, radioisotopes such as $^{125}I$, enzymes (e.g., peroxidase, alkaline phosphatase, beta-galactosidase, and glucose oxidase), enzyme substrates, luminescent substances, fluorescent substances, biotin, and colored substances. In binding these labeling agents to the antibody, the maleimide method (J. Biochem. (1976), 79, 233), the activated biotin method (J. Am. Chem. Soc. (1978), 100, 3585) or the hydrophobic bond method, for instance, can be used.

One can detect the duplication by using also antibodies that recognize regions of the CFTR protein up to the junction (i.e. E528), such that the truncated protein will display a molecular weight different from the full length normal CFTR protein.

One skilled in the art would readily recognize that the measurement of SEQ ID NO:1 or other unique C-terminal CFTR sequence can be in an ELISA which requires a specific antibody to the unique amino acid sequence, which antibody is readily available using standard methods known in the art. In the Western blot method, a protein mixture potentially containing the CFTR product with unique C-terminal amino acid sequence (e.g. SEQ ID NO:1) is subjected to gel electrophoresis, usually under denaturing conditions. The developed gel is then blotted with nitrocellulose paper to which the proteins in the gel adhere, maintaining relative positioning. The membrane is then blocked by being flooded with a protein solution, for example bovine serum albumin, in order to prevent non-specific protein interactions between the membrane and the antibody protein. The blocked nitrocellulose membrane is then incubated with a first (i.e., "primary") directed to the peptide of interest, for example SEQ ID NO: 1. After rinsing to remove unbound primary antibody, a secondary antibody, directed to the primary antibody, is introduced. The secondary antibody can be linked to an enzyme that can allow for visualization as, for example, by having specificity for a non-chromophoric substrate which turns colored after reaction with the enzyme linked to the secondary antibody. Other visualization methods known in the art include, without limitation, radioactivity and fluoroscence.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879-5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Other CF mutations that can be detected together with the detection of the exon 6b-10 duplication include those known under symbols: 2789+5G>A; 711+1G>T; W1282X; 3120+1G>A; d1507; dF508; (F508C, 1507V, 1506V); N1303K; G542X, G551D, R553X, R560T, 1717-1G>A: R334W, R347P, 1078delT; R117H, 1148T, 621+1G>T; G85E; R1162X, 3659delC; 2184delA; A455E, (5T, 7T, 9T); 3849+10kbC>T; and 1898+1G>A, are described in U.S. patent application Ser. No. 396,894, filed Apr. 22, 1989, application Serial No. 399,945, filed Aug. 29, 1989, application Serial No. 401,609 filed Aug. 31, 1989. and U.S. Pat. Nos. 6,011,588 and 5,981,178, which are hereby incorporated by reference in their entirety.

Still other CFTR mutations and PCR primer pairs for amplifying segments of the CFTR gene containing the mutations are shown in Table 3.

TABLE 3

CF mutations and associated amplification primers

| CF Mutation | Nucleotide Change | Forward and Reverse PCR Primers |
|---|---|---|
| S158T | 605G–>C | q4e1F and q4e1R |
| V358I | 1204G–>A | q7e3F and q7e4R |
| 119del6 | 1198-1202del (deletes TGGGCT and results in W356 and A357) | q7e3F and q7e4R |
| G451V | 1484G–>T | q9e9F and q9e11R |
| K481E | 1573A–>G | s10e3F and s10e2R |
| C491S | 1064G–>C | s10e3F and s10e2R |
| K503N + frameshift | 1641-1642AG–>T (deletes 1641A and 1642G and replaces with T) | s10e3F and s10e2R |
| 2949del5 | 2949-2953del (deletes TACTC) | q15e3F and q15e4R |
| H949L | 2798A–>T | q15e3F and q15e4R |
| T1036N | 3239C–>A | q17ae1F and q17ae1R |
| F1099L | 3429C–>A | q17be1F and q17be1R |

The primers for amplifying segments of the CFTR gene may hybridize to coding or non-coding CFTR sequences under stringent conditions. Preferred primers are those that flank mutant CF sequences. Primers for CF mutations in Table 3 are shown in Table 4.

TABLE 4

Amplification primer sequences for CF mutations

| CF Mutation | Forward and Reverse PCR Primers |
|---|---|
| S158T | q4e1F: (SEQ ID NO: 75) TGTAAAACGACGGCCAGTaaagtettgtgttgaaattct cagg |
| | q4e1R: (SEQ ID NO: 76) CAGGAAACAGCTATGACCCAGCTCACTACCTAATTTATG ACAT |
| V358I 119del6 | q7e3F: (SEQ ID NO: 77) TGTAAAACGACGGCCAGTcttccattccaagatccc |
| | q7e4R: (SEQ ID NO: 78) CAGGAAACAGCTATGACCGCAAAGTTCATTAGAACTGATC |
| G451V | g9e9F: (SEQ ID NO: 79) TGTAAAACGACGGCCAGTtggatcatgggccatgtgc and |
| | g9e11R: (SEQ ID NO: 80) CAGGAAACAGCTATGACCAAAGAGACATGGACACCAAAT TAAG |
| K481E C491S | s10e3F: (SEQ ID NO: 81) TGTAAAACGACGGCCAGTagcagagtacctgaaacagga |
| K503N + frame-shift | s10e2R: (SEQ ID NO: 82) CAGGAAACAGCTATGACCCATTCACAGTAGCTTACCCA |
| 2949de15 | q15e3F: (SEQ ID NO: 83) TGTAAAACGACGGCCAGTggttaagggtgcatgctatc |
| H949L | q15e4R: (SEQ ID NO: 84) CAGGAAACAGCTATGACCGGCCCTATTGATGGTGGATC |
| T1036N | q17ae1F: (SEQ ID NO: 85) TGTAAAACGACGGCCAGTacactttgtccactttgc |
| | q17ae1R: (SEQ ID NO: 86) CAGGAAACAGCTATGACCAGATGAGTATCGCACATTC |

TABLE 4-continued

Amplification primer sequences for CF mutations

| CF Mutation | Forward and Reverse PCR Primers |
|---|---|
| F1099L | q17be1F: (SEQ ID NO: 87) TGTAAAACGACGGCCAGTatctattcaaagaatggcac |
| | q17be1R: (SEQ ID NO: 88) CAGGAAACAGCTATGACCGATAACCTATAGAATGCAGC |

CF mutations in the amplified nucleic acid may be identified in any of a variety of ways well known to those of ordinary skill in the art. For example, if an amplification product is of a characteristic size, the product may be detected by examination of an electrophoretic gel for a band at a precise location. In another embodiment, probe molecules that hybridize to the mutant or wildtype CF sequences can be used for detecting such sequences in the amplified product by solution phase or, more preferably, solid phase hybridization. Solid phase hybridization can be achieved, for example, by attaching the CF probes to a microchip. Probes for detecting CF mutant sequences are well known in the art. See Wall et al. "A 31-mutation assay for cystic fibrosis testing in the clinical molecular diagnostics laboratory," Human Mutation, 1995; 5(4):333-8, which specifies probes for CF mutations ΔF508 (exon 1), G542X (exon 11), G551D (exon 11), R117H (exon 4), W1282X (exon 20), N1303K (exon 21), 3905insT (exon 20), 3849+10Kb (intron 19), G85E (exon 3), R334W (exon 7), A455E (exon 9), 1898+1 (exon 12), 2184delA (exon 13), 711+1 (exon 5), 2789+5 (exon 14b), Y1092x exon 17b), ΔI507 (exon 10), S549R(T-G) (exon 11), 621+1 (exon 4), R1162X (exon 19), 1717-1 (exon 11), 3659delC (exon 19), R560T (exon 11), 3849+4 (A-G) (exon 19), Y122X (exon 4), R553X (exon 11), R347P (exon 7), R347H (exon 7), Q493X (exon 10), V520F (exon 10), and S549N (exon 11).

CF probes for detecting mutations as described herein may be attached to a solid phase in the form of an array as is well known in the art (see, U.S. Pat. Nos. 6,403,320 and 6,406,844). For example, the full complement of 24 probes for CF mutations with additional control probes (30 in total) can be conjugated to a silicon chip essentially as described by Jenison et al., Biosens Bioelectron. 16(9-12):757-63 (2001) (see also U.S. Pat. Nos. 6,355,429 and 5,955,377). Amplicons that hybridized to particular probes on the chip can be identified by transformation into molecular thin films. This can be achieved by contacting the chip with an anti-biotin antibody or streptavidin conjugated to an enzyme such as horseradish peroxidase. Following binding of the antibody (or streptavidin)-enzyme conjugate to the chip, and washing away excess unbound conjugate, a substrate can be added such as tetramethylbenzidine (TMB) {3,3',5,5'Tetramethylbenzidinc} to achieve localized deposition (at the site of bound antibody) of a chemical precipitate as a thin film on the surface of the chip. Other enzyme/substrate systems that can be used are well known in the art and include, for example, the enzyme alkaline phosphatase and 5-bromo-4-chloro-3-indolyl phosphate as the substrate. The presence of deposited substrate on the chip at the locations in the array where probes are attached can be read by an optical scanner. U.S. Pat. Nos. 6,355,429 and 5,955,377, which are hereby incorporated by reference in their entirety including all charts and drawings, describe preferred devices for performing the methods of the present invention and their preparation, and describes methods for using them.

The binding of amplified nucleic acid to the probes on the solid phase following hybridization may be measured by methods well known in the art including, for example, optical detection methods described in U.S. Pat. No. 6,355,429. In preferred embodiments, an array platform (see, e.g., U.S. Pat. No. 6,288,220) can be used to perform the methods of the present invention, so that multiple mutant DNA sequences can be screened simultaneously. The array is preferably made of silicon, but can be other substances such as glass, metals, or other suitable material, to which one or more capture probes are attached. In preferred embodiments, at least one capture probe for each possible amplified product is attached to an array. Preferably an array contains 10, more preferably 20, even more preferably 30, and most preferably at least 60 different capture probes covalently attached to the array, each capture probe hybridizing to a different CF mutant sequence. Nucleic acid probes useful as positive and negative controls also may be included on the solid phase or used as controls for solution phase hybridization.

Another approach, variously referred to as PCR amplification of specific allele (PASA) (Sarkar, et al., 1990 *Anal. Biochem.* 186:64-68), allele-specific amplification (ASA) (Okayama, et al., 1989 *J. Lab. Clin. Med.* 114:105-113), allele-specific PCR (ASPCR) (Wu, et al. 1989 *Proc. Natl. Acad. Sci. USA.* 86:2757-2760), and amplification-refractory mutation system (ARMS) (Newton, et al., 1989 *Nucleic Acids Res.* 17:2503-2516). The method is applicable for single base substitutions as well as micro deletions/insertions. In general, two complementary reactions are used. One contains a primer specific for the normal allele and the other reaction contains a primer for the mutant allele (both have a common 2nd primer). One PCR primer perfectly matches one allelic variant of the target, but is mismatched to the other. The mismatch is located at/near the 3' end of the primer leading to preferential amplification of the perfectly matched allele. Genotyping is based on whether there is amplification in one or in both reactions. A band in the normal reaction only indicates a normal allele. A band in the mutant reaction only indicates a mutant allele. Bands in both reactions indicate a heterozygote. As used herein, this approach will be referred to as "allele specific amplification (ASA)."

Allele specific amplification can be used to detect the exons 6b through 10 duplication by using as the ASA primer, one that hybridizes partially across the junction. The extent of junction overlap can be varied to allow specific amplification. For example, most of the forward primer sequence is designed to hybridize upstream of the junction site with only a few nucleotides hybridizing on the downside of the junction site. One skilled in the art can establish conditions where such primer hybridizes specifically to the junction fragment. The ASA primer may be designed to hybridize to the forward or reverse strand. Amplification is achieved using a primer down stream of the ASA primer. This primer set will be able to amplify a fragment from nucleic acid containing the 6b through 10 duplication but not from normal DNA. This approach can be used independently of any other amplification or as a secondary step after long range amplification or junction amplification.

In yet another approach for detecting wildtype or mutant CF sequences in amplified DNA is single nucleotide primer extension or "SNuPE." SNuPE can be performed as described in U.S. Pat. No. 5,888,819 to Goelet et al., U.S. Pat. No. 5,846,710 to Bajaj, Piggee, C. et al. Journal of Chromatography A 781 (1997), p. 367-375 ("Capillary Electrophoresis for the Detection of Known Point Mutations by Single-Nucleotide Primer Extension and Laser-Induced Fluorescence Detection"); Hoogendoorn, B. et al., Human Genetics (1999) 104:89-93, ("Genotyping Single Nucleotide Polymorphism by Primer Extension and High Performance Liquid Chromatography"); and U.S. Pat. No. 5,885,775 to Haff et al. (analysis of single nucleotide polymorphism analysis by mass spectrometry). In SNuPE, one may use as primers such as those specified in Table 4.

Another method for detecting CF mutations includes the Luminex xMAP system which has been adapted for cystic fibrosis mutation detection by TM Bioscience and is sold commercially as a universal bead array (Tag-It™).

Still another approach for detecting wildtype or mutant CF sequences in amplified DNA is oligonucleotide ligation assay or "OLA" or "OL". The OLA uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241:1077-1080 and U.S. Pat. No. 4,998,617.

These above approaches for detecting wildtype or mutant CF sequence in the amplified nucleic acid is not meant to be limiting, and those of skill in the art will understand that numerous methods are known for determining the presence or absence of a particular nucleic acid amplification product.

Multiplex amplification as described herein may include primers for amplifying one or more non-CFTR gene segments as an internal control. Such internal controls may include exon 1 of the coagulation factor 2 gene of chromosome 11 ("F2"), exon 10 of coagulation factor V of chromosome 11 ("F5") and/or exon 7 of the Tay Sachs HEXA gene of chromosome 15 ("TS"). In a preferred embodiment, all three of these exons may be amplified. Thus, the method can evaluate by a single multiplex PCR, a total of at least 32 target segments, the segments representing 27 exons of the CFTR gene, the CFTR promoter region, UpEx9 and three internal control exons.

To assist in identifying amplified segments, at least one primer from some or all of the primer pairs in the multiplex can be labeled with a detectable moiety. It would be evident to the skilled artisan that the detectable moiety could be attached in any manner of variety that does not interfere with the oligonucleotide to function as an amplification primer.

The phrase "detectable moiety" is used herein to denote any molecule (or combinations of molecules) that may be attached or otherwise associated with a molecule so that the molecule can be detected indirectly by detecting the detectable moiety. A detectable moiety can be a radioisotope (e.g., iodine, indium, sulfur, hydrogen etc.) a dye or fluorophor (e.g., cyanine, fluorescein, rhodamine), protein (e.g., avidin, antibody), enzyme (peroxidase, phosphatase, etc.), or any other agent that can be detected directly or indirectly. An enzyme is an example of a detectable moiety detected by indirect means. In this case, the enzyme is attached to the target nucleic acid and the presence of the enzyme is detected by adding an appropriate substrate that when acted upon by the enzyme, causes the substrate to change in color or to release a cleavage product that provides a different color from the original substrate.

The term "fluorescent detectable moiety" or "fluorophore" as used herein refers to a molecule that absorbs light at a particular wavelength (excitation frequency) and subsequently emits light of a longer wavelength (emission frequency). A fluorescent detectable moiety can be stimulated by a laser with the emitted light captured by a detector. The detector can be a charge-coupled device (CCD) or a confocal microscope, which records its intensity.

A useful detectable moiety is a cyanine dye such as Cy-5 and Cy-3, FAM, HEX, and the like. A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al. Donor/acceptor pairs of dyes that can be used include, for example, fluorescein/tetramethylrohdamine, IAEDANS/fluroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Other dyes include Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

In another embodiment, signal amplification may be achieved using labeled dendrimers as the detectable moiety (see, e.g., *Physiol Genomics* 3:93-99, 2000). Fluorescently labeled dendrimers are available from Genisphere (Montvale, N.J.). These may be chemically conjugated to the oligonucleotide primers by methods known in the art.

In another aspect the present invention provides kits for one of the methods described herein. The kit optionally contain buffers, enzymes, and reagents for amplifying the CFTR nucleic acid via primer-directed amplification. The kit also may include one or more devices for detecting the presence or absence of particular mutant CF sequences in the amplified nucleic acid. Such devices may include one or more probes that hybridize to a mutant CF nucleic acid sequence, which may be attached to a bio-chip device, such as any of those described in U.S. Pat. No. 6,355,429. The bio-chip device optionally has at least one capture probe attached to a surface on the bio-chip that hybridizes to a mutant CF sequence. In preferred embodiments the bio-chip contains multiple probes, and most preferably contains at least one probe for a mutant CF sequence which, if present, would be amplified by a set of flanking primers. For example, if five pairs of flanking primers are used for amplification, the device would contain at least one CF mutant probe for each amplified product, or at least five probes. The kit also preferably contains instructions for using the components of the kit.

The following examples serve to illustrate the present invention. These examples are in no way intended to limit the scope of the invention

EXAMPLES

Example 1: Sample Collection and Preparation

Whole Blood:

5 cc of whole blood is collected in a lavender-top (EDTA) tube or yellow-top (ACD) tube, Green-top (Na Heparin) tubes are acceptable but less desirable. DNA is extracted from blood. 100 ng or more DNA is prepared in TE or sterile water.

Amniotic Fluid:

10-15 cc of Amniotic Fluid is collected in a sterile plastic container.

Cultured Cells:

Two T-25 culture flasks with 80-100% confluent growth may be used.

Chorionic Villi:

10-20 mg of Chorionic Villi are collected in a sterile container. 2-3 mL of sterile saline or tissue culture medium is added.

Transport:

Whole Blood, Amniotic Fluid, Cultured Cells and Chorionic Villi can be shipped at room temperature (18°-26° C.). Amniotic Fluid, Cultured Cells or Chorionic Villi preferably is used without refrigeration or freezing. Whole Blood and Extracted DNA can be shipped at 2°–10° C.

Storage:

Whole Blood, Amniotic Fluid and Extracted DNA are stored at 2°-10° C., Cultured Cells and Chorionic Villi are stored at room temperature (18°-26° C.).

Stability:

Whole Blood is generally stable for 8 days at room temperature (18°-26° C.) or 8 days refrigerated at 2°–10° C. Amniotic Fluid, Cultured Cells, and Chorionic Villi are generally processed to obtain DNA within 24 hours of receipt. Extracted DNA is stable for at least 1 year at 2°-10° C.

Example 2: Amplification from DNA

Polymerase chain reaction (PCR) primer pairs were designed using the CFTR gene sequences in EMBL/Genbank (Accession Nos. M55106-M55131). Each PCR primer for the 32 separate PCR reactions contains either an M13 forward linker sequence or an M13 reverse linker sequence as appropriate to allow universal sequence reaction priming. Individual PCR reactions are performed in 96-well microtiter plates under the same conditions for each amplicon. Subsequently, the PCR products are purified with the Millipore Montage™ $PCR_{96}$ Cleanup kit (Millipore, Bedford, Mass.) on a Beckman BioMek 2,000 biorobot. Further details are provided in Strom et al., 2003 *Genetics in Medicine* 5(1):9-14.

In general, individual amplifications are prepared in a volume of 13.5 μl, which is added to the 96 well microtiter plates. Each amplification volume contained 2 μl of the nucleic acid sample (generally 10-100 ng of DNA), 11.5 μl of PCR-Enzyme Mix (PCR-Enzyme mix stock is prepared with 11.3 μl master mix, 0.25 μl $MgCl_2$ (from 25 mM stock), and 0.2 μl of FasStar Taq (source for last two reagents was Roche Applied science, Cat. No. 2 032 937). Master mix contained primers, Roche PCR buffer with $MgCl_2$, Roche GC rich solution (cat. No. 2 032 937), bovine serum albumin (BSA) (New England BioLabs, Cat no. B9001B), and NTPs (Amersham Biosciences, Cat no. 27-2032-01).

The final concentration in the PCR for $MgCl_2$ was 2.859 mM, for BSA is 0.725 μg/μl, and for each dNTP is 0.362 mM. Primer final concentrations varied from about 0.29 μM to about 0.036 μM PCR is conducted using the following temperature profile: step 1: 96° C. for 15 minutes; step 2: 94° C. for 15 seconds; step 3: decrease at 0.5° C./second to 56° C.; step 4: 56° C. for 20 seconds; step 5: increase at 0.3° C./second to 72° C., step 6: 72° C. for 30 seconds; step 7: increase 0.5° C. up to 94° C.; step 8: repeat steps 2 to 7 thirty three times; step 9: 72° C. for 5 minutes; step 10: 4° C. hold (to stop the reaction).

Example 3: Detection of CF Mutations

The purified PCR products are diluted to approximately 10 ng/L and cycle sequencing reactions are performed with an ABI Prism Big Dye™ Terminator v3.0 cycle sequencing reaction kit (Applied Biosystems, Foster City, Calif.) according to the manufacturer's protocol. The DNA primers used for the sequencing reaction are M13 forward and reverse primers as appropriate. Big Dye™ Terminator reaction products are purified by the Millipore Montage™ $Seq_{96}$ Sequencing Reaction Cleanup kit on a biorobot and analyzed on an ABI Prism 3100 Genetic Analyzer. Sequences obtained are examined for the presence of mutations by using ABI SeqScape v1.1 software. Both strands of DNA are sequenced.

All PCR reactions, purifications, and cycle sequencing reactions are performed in 96-well microtiter plates using biorobots to avoid errors introduced by manual setups. Loading of samples onto the capillary sequencer is also automated. One plate is sufficient to perform the entire sequencing reaction for a single patient. Theoretically, if all reactions were successful, the entire sequences for a single patient could be obtained in 24-48 hours after receipt of blood. In practice, however, one or more reactions must be repeated because of frequent polymorphisms in intron 8 and 6a and failed reactions.

Example 4: Multiplex PCR Assay for CFTR Gene Segments

A. Extraction of DNA

Whole blood, amniotic fluid, cultured cells, and chorionic villi, are maintained preferably under ambient temperature (18-26° C.). Whole blood should be stable for 8 days at ambient temperature (18-26° C.) or 8 days refrigerated (2-8° C.). Optimally, DNA should be extracted amniotic fluid, cultured cells, or chorionic villi within 24 hours of receipt. Samples are preferably analyzed without freezing. Once extracted, DNA should be stable for 24-48 hours at 2-8° C. DNA should be frozen if longer storage is anticipated.

The following example describes a suitable procedure to prepare nucleic acids from blood. 50 μL of whole blood is mixed with 0.5 ml of TE (10 mM Tris HCl, 1 mM EDTA, pH 7.5) in a 1.5 mL microfuge tube. The sample is spun for 10 seconds at 13,000×g. The pellet is resuspended in 0.1 mL of TE buffer with vortexing, and pelleted again. This procedure is repeated twice more, and then the final cell pellet is resuspended in 100 μl of K buffer 50 mM KCl, 10 mM Tris HCl, 2.5 mM $MgCl_2$, 0.5% Tween 20, 100 μg/mL proteinase K, pH 8.3) and incubated 45 minutes at 56° C., then 10 minutes at 95° C. to inactivate the protease.

Alternative nucleic acid extraction methods can be used such as the Qiagen extraction method (Qiagen BioRobot 9604).

B. Preparation of CFTR-Multiplex PCR Primer Mix

A multiplex PCR that can verify a suspected CFTR promoter deletion or duplication and assess the extent of such deletion or duplication may be performed using the mixture of primers shown in Table 5. The amount of each primer in the amplification is listed in Table 5 along with the expected size of the fragment. The promoter deletion/duplication verification PCR primer mix (1,025 μL) was made by mixing stock solutions (100 μM) of each of the primers shown in Table 5. The sequences of these primers can be found in Tables 1 and 2. In addition to the three promoter primers upstream of the first promoter primer set, the master mix includes primers for the three internal controls and primer pairs for CFTR exons 1-4.

TABLE 5

CFTR promoter deletion/duplication verification primer master mix.

| Primer Name | x 1 rxn (ul) | 200 | Final Conc in PCR Reaction uM | Size Expected |
|---|---|---|---|---|
| TSF | 0.05 | 10 | 0.2 | 140 |
| TSR | 0.05 | 10 | 0.2 | |
| F2F | 0.05 | 10 | 0.2 | 332 |
| F2R | 0.05 | 10 | 0.2 | |
| F5F | 0.05 | 10 | 0.2 | 212 |
| F5R | 0.05 | 10 | 0.2 | |
| UpPr1F | 0.05 | 10 | 0.2 | 230 |
| UpPr1R | 0.05 | 10 | 0.2 | |
| CFDEL3F2 | 0.025 | 5 | 0.1 | 132 |
| CFDEL3R | 0.025 | 5 | 0.1 | |
| UpPr2F1 | 0.025 | 5 | 0.1 | 202 |
| UpPr2R | 0.025 | 5 | 0.1 | |
| CFDEL2F | 0.025 | 5 | 0.1 | 154 |
| CFDEL2R | 0.025 | 5 | 0.1 | |
| UpPr3F | 0.025 | 5 | 0.1 | 188 |
| UpPr3R | 0.025 | 5 | 0.1 | |
| CFDEL4F | 0.0375 | 7.5 | 0.15 | 237 |
| CFDEL4R | 0.0375 | 7.5 | 0.15 | |
| CFDEL1F | 0.075 | 15 | 0.3 | 272 |
| CFDEL1R | 0.075 | 15 | 0.3 | |
| CFDELPF | 0.075 | 15 | 0.3 | 287 |
| CFDELPR | 0.075 | 15 | 0.3 | |
| Total | 1.025 | 205 | | |

C. Amplification from DNA

Individual amplifications were prepared in a volume of 25 μl. Each amplification volume contained 4 μl of the DNA sample (generally 10-100 ng of DNA), 20.6 μl of CFTR Master Mix, and 0.4 μl of FasStar Taq (Roche Applied science, Cat. No. 2 032 937). In another approach, individual amplifications were prepared in a volume of 12.5 μl. Each amplification volume contained 2 μl of the DNA sample (generally 10-100 ng/μl of DNA), 10.3 μl of CFTR master mix and 0.2 μl of FasStar Taq (Roche Applied Science, Cat no. 2032937).

Master mix contained the CFTR-multiplex PCR primer mix, Roche PCR buffer with $MgCl_2$, Roche GC rich solution (cat. No. 2 032 937), bovine serum albumin (BSA) (New England BioLabs, Cat no. B9001B), and NTPs (Amersham Biosciences, Cat no. 27-2032-01). The final concentration in the PCR for $MgCl_2$ was 2.859 mM, for BSA was 0.725 μg/μl, and for each dNTP was 0.362 mM. The PCR master mix for the full multiplex of primers in Table 1 is shown in Table 6. The PCR master mix for the full multiplex of promoter region primers and controls in Tables 2 is shown in Table 7. The concentration of individual primers fell in the range 0.1 to 0.4 μM.

TABLE 6

| CFTR PCR master mix | | | |
|---|---|---|---|
| Reagent | X 1 rxn (ul) | 1000 | Final Conc in PCR Reaction mM |
| FS 10X w/o $MgCl_2$ | 5 | 5000 | 2X |
| $MgCl_2$ | 4 | 4000 | 4 |
| 25 mM dNTP | 0.4 | 400 | 0.4 |
| Primer MIX | 4.55 | 4550 | |
| GC rich | 2.5 | 2500 | 1X |
| BSA (10 mg/ml) | 1 | 1000 | 0.4 ug/ul |
| Water | 3.15 | 3150 | |
| Total | 20.6 | 20600 | |

TABLE 7

| CFTR Promoter region Master mix | | | |
|---|---|---|---|
| Reagent | x 1 rxn (ul) | 200 | Final Conc in PCR Reaction mM |
| FS 10X w/o MgCl2 | 2.5 | 500 | 2X |
| MgCl2 | 2 | 400 | 2 |
| 25 mM dNTP | 0.2 | 40 | 0.2 |
| Primer MIX | 1.025 | 205 | |
| GC rich | 1.25 | 250 | 1X |
| BSA (10 mg/ml) | 0.5 | 100 | 0.4 ug/ul |
| Water | 2.825 | 565 | |
| Total | 10.3 | 2060 | |

PCR was conducted using the following temperature profile: step 1: 95° C. for 5 minutes; step 2: 94° C. for 15 seconds; step 3: decrease at 0.5° C./second to 56° C.; step 4: 56° C. for 1 minute and 10 seconds; step 5: increase at 0.5° C./second to 72° C., step 6: 72° C. for 45 seconds+5 seconds additional per additional cycle; step 7: increase 0.5° C. up to 94° C.; step 8: repeat steps 2 to 7 twenty one times; step 9: 72° C. for 5 minutes; step 10: 60° C. for 75 min, step 11: 4° C. hold (to stop the reaction).

D. Detection and Analysis of Amplified Product

2 μL of each PCR product was added to 10.5 μL Hi-Di-Rox 350 mix and loaded onto a ABI 3100 Genetic Analyzer for separation. Alternatively, electrophoresis can be performed by subjecting the amplified product to gel electrophoresis such as an agarose gel electrophoresis. The primers may need to be labeled with a detectable label to enhance the sensitivity of detection in some gel systems.

The data corresponding to the amplified nucleotide segments from the ABI3100 were analyzed using GeneMapper software. The observed size and color of each target segment amplified from normal DNA using the primer set shown in Table 1 is shown in Table 8. FAM is blue and HEX is green.

TABLE 8

| Analysis of amplified CFTR exons and internal controls | | | |
|---|---|---|---|
| CFTR exon/intron or internal control | Size | Observed size | DYE |
| UpEx 9 | 118 | 113.6 | Green |
| Ex 3 | 128 | 124.2 | Blue |
| Ex 11 | 132 | 127.2 | Blue |
| Ex 21 | 136 | 132.7 | Blue |
| Tay-Sachs | 140 | 137.6 | Green |
| Ex 14a | 144 | 142.1 | Blue |
| Ex 2 | 154 | 153 | Blue |
| Ex 5 | 159 | 157.4 | Blue |
| Ex 20 | 162 | 161.8 | Blue |

TABLE 8-continued

| Analysis of amplified CFTR exons and internal controls | | | |
|---|---|---|---|
| CFTR exon/intron or internal control | Size | Observed size | DYE |
| Ex 6a | 170 | 170.4 | Blue |
| Ex 22 | 176 | 176.6 | Blue |
| Ex 24 | 187 | 183.6 | Blue |
| Ex 17a | 190 | 188.4 | Blue |
| Ex 23 | 193 | 191.6 | Blue |
| Ex 14b | 201 | 200.3 | Blue |
| Ex 12 | 208 | 205.9 | Blue |
| Factor 5 | 212 | 210.4 | Green |
| Ex 8 | 216 | 215 | Blue |
| Ex 6b | 228 | 226.8 | Blue |
| Ex 4 | 237 | 236.9 | Blue |
| Ex 10 | 245 | 245.5 | Blue |
| Ex 19 | 250 | 248.7 | Blue |
| Ex 13 | 253 | 253.3 | Blue |
| Ex 15 | 262 | 261.6 | Blue |
| Ex 7 | 267 | 267.1 | Blue |
| Ex 1 | 272 | 272 | Blue |
| Ex 16 | 281 | 280.9 | Blue |
| Promoter | 287 | 288.2 | Blue |
| Ex 18 | 297 | 296.1 | Blue |
| Ex 17b | 306 | 303.9 | Blue |
| Ex 9 | 318 | 317.4 | Blue |
| Factor 2 | 332 | 331.9 | Blue |

The signal for each of the above amplicons observed for DNA from a sample with an unknown CFTR genotype is compared with the amount of the corresponding amplified segment observed for DNA from an individual with a wildtype CFTR gene. The GeneMapper software is used to analyze data generated from the ABI 3100. An Excel report is uploaded into a database that will score the results and generate automated allele calls.

A deletion of one or more exons will be shown by a drop in the intensity of the fragment(s) by at least 30-50%, of the normal (wildtype CFTR exon) signal while a duplication will show an increase to at least 130-150% of the normal (wildtype CFTR exon) signal.

For best results, sample DNA for unknown CFTR genotype should be amplified in parallel with positive control sample containing wt/wt CFTR genotype and/or wt/mut genotype for CF carriers.

Negative controls included;

a) NS Control: a reagent blank (NS control) comprises all reagents and processing used to prepare sample DNA but without any starting DNA; and b) ND Control: A minus DNA control (ND control) is used which consists of a PCR kit and polymerase mix used for the assay run.

Positional Control: a QC blank is placed randomly within each plate to ensure results reflect the correct positioning of the Extraction/PCR plate for detection.

Negative controls should display no significant amplification and/or fluorescent signal. If the reagent blank (NS control) shows evidence of significant amplification, all the patient samples associated with that NS control are potentially contaminated. If the minus DNA control (ND control) yields significant amplification, the PCR amplification reagents are potentially contaminated. Note that the existing PCR master reaction mix may be the source of the contamination. Specimens my need to be re-extracted and re-assayed (NS) and the entire assay repeated (ND).

Negative control DNAs should display no significant fluorescent signal upon electrophoresis on an ABI3100 genetic analyzer. If the NS control shows evidence of significant fluorescence, all the patient samples associated with that NS control are potentially contaminated.

The QC Blank control should display no significant signal.

Example 5: Evaluating Samples from Individuals to Determine a Genetic Basis for CF Samples from patients with a mutant CF gene were evaluated for CF deletion or duplication analysis in accordance with the methods herein. Several samples with rearrangements were identified. A deletion encompassing the CFTR promoter, and exons 1 and 2 was detected in one sample, with the same mutation detected in the maternal DNA. In another family, a deletion of the promoter and exon 1 was detected in three siblings. In both of these cases, the families were African-American, and a 3120+1G>A splice site mutation was identified. These deletions have not been previously described. In a third case involving a Caucasian patient, a deletion of exons 17a, 17b and 18 was identified and the same mutation was detected in the paternal DNA. In four other cases, deletions in exons 2 and 3; exons 4, 5 and 6a; exons 17a and 17b; and a deletion of exons 22, 23 and 24 were identified. These mutations would remove parts of transmembrane domain 1, transmembrane domain 2, or the second Nucleotide Binding Domain. In patients diagnosed with "classic CF" submitted for sequencing analysis, 20% harbored rearrangements, accounting for 10% of CF chromosomes. Classic CF is characterized by elevated sweat chloride, lung and pancreatic insufficiency, failure to thrive, and in most male cases, and congenital bilateral absence of the vas deferens (CBAVD). The frequency of occurrence of rearrangements in CF patients when only one mutation is identified by DNA sequencing is 50%. It is possible that complex abnormalities may account for a significant proportion of CF chromosomes in the general population.

Example 6: Clinical Presentation of Dup Ex 6b-10 (IVS6a+415 IVS10+2987Dup26817 bp)

Phenotype details: The patient is a 19 year old, Caucasian female with a diagnosis of cystic fibrosis. She was born with meconium ileus and has an elevated sweat chloride test of 110, pulmonary disease and liver cirrhosis. She had a similarly affected sister who is deceased. Previous mutation testing had revealed the heterozygous presence of deltaF508 that was inherited from her mother. DNA Sequencing did not identify second mutation, Analysis by SQF PCR of fragments representing the promoter and all CFTR exons identified a tandem duplication of exons 6b-10. DNA Sequencing verified the presence of the duplication by detecting a fusion of IVS10 to IVS6a.

Nucleotide change: A duplication of exons 6b-10. The duplication is 26,817 bp long.

Exon: Duplication of Exons 6b-10.

Consequence: Out-of-frame fusion of exon 10 to exon 6b. The duplication would cause an out-of-frame addition if 8 amino acids after codon E528 of Exon 10, followed by a TGA Stop codon. The result is a truncated protein lacking terminal NBD1 and beyond.

Example 7: Detecting Dup Ex 6b-10 with Primers Flanking the Junction Site

This example demonstrates identification of the exon 6b-10 mutation in nucleic acid from the patient discussed in Example 6. FIG. 2 shows a schematic of the CFTR gene with arrows depicting the general location of forward and reverse PCR primers flanking the unique junction IVS10+2,987/IVS6a+415. PCR across the junction was achieved using a forward primer from exon 10 located in intron 9 (5'-TGTAAAACGACGGCCAGTagcagagtacctgaaacagga-3'; SEQ ID NO: 89) and a reverse primer for exon 6b located in intron 6b (5'-CAGGAAACAGCTATGACCGTGGAAGTCTACCATGATAAACATA-3'; SEQ ID NO: 90). Following PCR a single product was observed on an agarose gel, running just below a 4.6 kb standard.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

I claim:

1. A kit comprising:

(i) a forward primer that comprises the sequence of SEQ ID NO: 89; and (ii) a reverse primer that comprises the sequence of SEQ ID NO: 90, wherein the forward primer or reverse primer is detectably labeled.

2. The kit of claim 1, further comprising a nucleic acid probe that binds to an amplification product produced by the forward primer and the reverse primer.

3. The kit of claim 2, wherein the nucleic acid probe is detectably labeled.

4. The kit of claim 2, wherein the nucleic acid probe spans a junction site between exons 10 and 6b resulting from a duplication of exon 6b through exon 10 of the CFTR gene.

5. The kit of claim 2, wherein the nucleic acid probe spans a IVS10+2,987/IVS6a+415 junction site.

6. The kit of claim 2, wherein the nucleic acid probe comprises the sequence of SEQ ID NO:2.

7. The kit of claim 2, wherein the nucleic acid probe comprises the sequence of SEQ ID NO:3.

8. The kit of claim 2, wherein the nucleic acid probe comprises the sequence of SEQ ID NO:4.

9. The kit of claim 1, wherein the forward primer and/or reverse primer are detectably labeled with a fluorescent dye.

10. The kit of claim 2, wherein the nucleic acid probe is detectably labeled with a fluorescent dye.

11. The kit of claim 1, wherein the forward primer and reverse primer are present together in an amplification master mix that further comprises DNA polymerase, dNTPs and PCR buffer.

12. A kit comprising:

(a) a primer pair comprising (i) a forward primer that comprises the sequence of SEQ ID NO: 89; and (ii) a reverse primer that comprises the sequence of SEQ ID NO: 90; and (b) a detectably labeled nucleic acid probe that that binds to an amplification product produced by the forward primer and the reverse primer.

13. The kit of claim 12, wherein the detectably labeled nucleic acid probe spans a junction site between exons 10 and 6b resulting from a duplication of exon 6b through exon 10 of the CFTR gene.

14. The kit of claim 12, wherein the detectably labeled nucleic acid probe spans a IVS10+2,987/IVS6a+415 junction site.

15. The kit of claim 12, wherein the detectably labeled nucleic acid probe comprises the sequence of SEQ ID NO: 2, 3, or 4.

16. The kit of claim 12, wherein the forward primer, reverse primer, and/or probe are present together in an amplification master mix that further comprises DNA polymerase, dNTPs and PCR buffer.

17. The kit of claim 12, wherein the nucleic acid probe is detectably labeled with a fluorescent dye.

18. The kit of claim 12, wherein the forward primer and/or reverse primer are detectably labeled with a fluorescent dye.

* * * * *